US009815752B2

United States Patent
Hossain et al.

(10) Patent No.: US 9,815,752 B2
(45) Date of Patent: Nov. 14, 2017

(54) FLUIDIZABLE CATALYST FOR OXIDATIVE DEHYDROGENATION OF ALKANES TO OLEFINS IN AN OXYGEN FREE ENVIRONMENT

(71) Applicant: KING FAHD UNIVERSITY OF PETROLEUM AND MINERALS, Dhahran (SA)

(72) Inventors: Mohammad Mozahar Hossain, Dhahran (SA); AbdAlwadood Hassan Elbadawi, Dhahran (SA); Shaikh Abdur Razzak, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 15/042,703

(22) Filed: Feb. 12, 2016

(65) Prior Publication Data
US 2017/0233312 A1   Aug. 17, 2017

(51) Int. Cl.
*C07C 5/42*    (2006.01)
*B01J 23/22*   (2006.01)
(Continued)

(52) U.S. Cl.
CPC .............. *C07C 5/42* (2013.01); *B01J 23/22* (2013.01); *B01J 35/0026* (2013.01);
(Continued)

(58) Field of Classification Search
CPC ... B01J 21/04; B01J 23/10; B01J 23/20; B01J 23/22; B01J 23/92; B01J 35/0026;
(Continued)

(56) References Cited

U.S. PATENT DOCUMENTS 3,207,808 A * 9/1965 Bajars ................... C07C 5/56
                                            502/224
3,786,001 A * 1/1974 Cornelius et al. ....... B01J 11/12
                                            208/124
(Continued)

FOREIGN PATENT DOCUMENTS

CN    10 4248982    * 12/2014    ............. B01J 23/10
WO    2014/035590 A1    3/2014

OTHER PUBLICATIONS

"Oxidative dehydrogenation of ethane to ethylene over V2O5/Nb2O5 catalysts," A. Qiao et al. Catalysis Communications 30 (2013), pp. 45-50.*

(Continued)

*Primary Examiner* — Patricia L. Hailey
(74) *Attorney, Agent, or Firm* — Oblon, McClelland, Maier & Neustadt, L.L.P.

(57) ABSTRACT

Fluidizable catalysts for the oxygen-free oxidative dehydrogenation of alkanes to corresponding olefins. The catalysts comprise 10-20% by weight per total catalyst weight of one or more vanadium oxides ($VO_x$) such as $V_2O_5$ as well as 1-5% by weight per total catalyst weight of niobium as a promoter. The dehydrogenation catalysts are mounted on an alumina support that is modified with lanthanum to stabilize bulk phase transformation of the alumina. Various methods of preparing and characterizing the catalysts as well as methods for the oxygen-free oxidative dehydrogenation of alkanes to corresponding olefins with improved alkane conversion and olefin selectivity are also disclosed.

18 Claims, 9 Drawing Sheets

(51) Int. Cl.
     B01J 35/10    (2006.01)
     B01J 35/02    (2006.01)
     B01J 35/00    (2006.01)
     B01J 37/04    (2006.01)
     B01J 37/18    (2006.01)
     B01J 37/14    (2006.01)
(52) U.S. Cl.
     CPC ......... B01J 35/023 (2013.01); B01J 35/1014
             (2013.01); B01J 37/04 (2013.01); B01J 37/14
                     (2013.01); B01J 37/18 (2013.01); C07C
                 2521/04 (2013.01); C07C 2523/22 (2013.01)
(58) Field of Classification Search
     CPC ...... B01J 35/0053; B01J 35/06; B01J 35/023;
                 B01J 35/1014; B01J 37/02; B01J 37/04;
                 B01J 37/14; B01J 37/18; C07C 2521/04;
                     C07C 2523/10; C07C 2523/20; C07C
                                                  2523/22
     USPC .................................................. 502/303, 354
     See application file for complete search history.

(56)              References Cited

U.S. PATENT DOCUMENTS 5,556,825 A  *  9/1996  Shelef .................. B01D 53/945
                                                          423/213.5
     6,566,573 B1    5/2003  Bharadwaj et al.
     7,145,051 B2   12/2006  Ou et al.

2003/0166984 A1 *  9/2003  Park ...................... C07C 5/3332
                                                               585/444
     2005/0081443 A1 *  4/2005  Aiello ................. B01D 53/864
                                                              48/198.3
     2005/0272965 A1   12/2005  Watson et al.
     2013/0072737 A1    3/2013  Kustov et al.
     2013/0178670 A1 *  7/2013  Zhou .................... B01J 37/0205
                                                               568/885
     2017/0008821 A1 *  1/2017  Hossain ................ C07C 5/3332

OTHER PUBLICATIONS

Richard Blom, et al., "Carbon dioxide reforming of methane over lanthanum-modified catalysts in a fluidized-bed reactor", Catalyst Today, http://www.sciencedirect.com/science/article/pii/0920586194801770, vol. 21, Issue 2-3, Dec. 1994, 1 page.

S. Al-Ghamdi, et al., "$VO_x$/c-$Al_2O_3$ catalyst for oxidative dehydrogenation of ethane to ethylene: Desorption kinetics and catalytic activity", Applied Catalysis A: General, vol. 450, (2013), pp. 120-130.

Idris A. Bakare, et al., "Fluidized bed ODH of ethane to ethylene over $VO_x$-$MoO_x$/γ-$Al_2O_3$ catalyst: Desorption kinetics and catalytic activity", Chemical Engineering Journal, vol. 278, (2015), pp. 207-216.

AbdAlwadood H. Elbadawi, et al., "Reduction kinetics and catalytic activity of $VO_x$/γ-$Al_2O_3$-$ZrO_2$ for gas phase oxygen free ODH of ethane", Chemical Engineering Journal, vol. 284, (2016), pp. 448-457.

* cited by examiner

FLUIDIZABLE CATALYST FOR OXIDATIVE DEHYDROGENATION OF ALKANES TO OLEFINS IN AN OXYGEN FREE ENVIRONMENT

BACKGROUND OF THE INVENTION

Technical Field

The present disclosure relates to fluidizable vanadium based $VO_x$—Nb/La—$Al_2O_3$ catalysts for the oxidative dehydrogenation of alkanes in the absence of gas phase oxygen.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Ethylene is a starting material for several industrial syntheses. It is used as an important intermediate in the chemical industry, as well as to produce polyethylene [S. A. R. Mulla, O. V. Buyevskaya, and M. Baerns, "A comparative study on non-catalytic and catalytic oxidative dehydrogenation of ethane to ethylene," vol. 226, pp. 73-78, 2002.]. Conventionally, ethylene is produced by cracking processes (mainly steam cracking). However, these processes require high energy consumption, which contributes to a high production cost. Alternatively, catalytic oxidative dehydrogenation (ODH) is an emerging technology which can eliminate some of the drawbacks associated with conventional cracking processes. Since oxidative dehydrogenation catalysts play an important role in such reactions, much ongoing research work focuses on different aspects of the catalysis. These aspects include catalyst active phases, structure and morphology which all are responsible for catalyst performance. Furthermore, in the area of oxidative dehydrogenation of ethane catalyst selectivity can be one of the most important factors effecting performance, in addition to catalyst stability and other parameters.

Supported metal oxides are common catalysts for oxidative dehydrogenation reactions, and modifying the catalyst support is an effective way to enhance performance. It has been established that the support can have a major effect on catalyst performance. For instance, vanadium (V) and chromium (Cr) oxides on different supports have been tested [M. Loukah, J. C. Vedrine, and M. Ziyad, "Oxidative dehydrogenation of ethane on V- and Cr-based phosphate catalysts," vol. 4, 1995.]. It was reported that at an equivalent conversion extent, ethylene selectivity followed the order of $VO_2P_2O_7$>$CrPO_4$>$Cr/\alpha\text{-}ZrP$>$Cr/\beta\text{-}ZrP$. In addition, $TiO_2$ supported $VOPO_4$ catalysts have shown good selectivity in the oxidative dehydrogenation of ethane demonstrating higher ethylene productivity than that reported for $(VO)_2P_2O_7$ [P. Ciambelli, P. Galli, L. Lisi, M. A. Massucci, P. Patrono, R. Pirone, G. Ruoppolo, and G. Russo, "TiO 2 supported vanadyl phosphate as catalyst for oxidative dehydrogenation of ethane to ethylene," vol. 203, pp. 133-142, 2000.—incorporated herein by reference in its entirety]. Furthermore, iron phosphate phases have also been considered, such as $FePO_4$, $Fe_2P_2O_7$, $\alpha\text{-}Fe_3(P_2O_7)$ and $\beta\text{-}Fe_3(P_2O_7)$ [J. E. Miller, M. M. Gonzales, L. Evans, A. G. Sault, C. Zhang, R. Rao, G. Whitwell, A. Maiti, and D. King-Smith, "Oxidative dehydrogenation of ethane over iron phosphate catalysts," Appl. Catal. A Gen., vol. 231, no. 1-2, pp. 281-292, May 2002.—incorporated herein by reference in its entirety]. Nickel (Ni) and Ni—Co/$Al_2O_3$ powder catalysts have also been investigated and were found active and selective for this reaction but with lower conversion and less selectivity (less than 30%) [J. P. Bortolozzi, L. B. Gutierrez, and M. a. Ulla, "Synthesis of Ni/$Al_2O_3$ and Ni—Co/$Al_2O_3$ coatings onto AISI 314 foams and their catalytic application for the oxidative dehydrogenation of ethane," Appl. Catal. A Gen., vol. 452, pp. 179-188, February 2013.—incorporated herein by reference in its entirety].

Catalysts such as AlPO-34, SAPO-34, NaAPSO-34 and LaAPSO-34 were also studied for oxidative dehydrogenation, and it was observed that cracking reactions are inhibited on SAPO-34 catalysts where deactivation effects were practically absent even after a 12 hour experiment. When metals such as vanadium (V), cobalt (Co), magnesium (Mg) or manganese (Mn) are introduced to the ALPO-5 structure good activity is obtained at temperatures of 425-600° C. However, ethylene selectivity did not exceed 65% at 7.5% ethane conversion, and the contact time used was greater than that used for the SAPO-34 based catalysts [L. Marchese, "Acid SAPO-34 Catalysts for Oxidative Dehydrogenation of Ethane," J. Catal., vol. 208, no. 2, pp. 479-484, June 2002.]. Vanadium with titanium (Ti), tin (Sn) or zirconium (Zr) pyrophosphates support were also studied in the oxidative dehydrogenation reaction, and exhibited a good conversion (20%) and selectivity (over 90%) at 560° C. Notably, this performance is again related to vanadium (V) as a surface species [L. Lisi, G. Ruoppolo, M. P. Casaletto, P. Galli, M. a. Massucci, P. Patrono, and F. Pinzari, "Vanadium-metal(IV)phosphates as catalysts for the oxidative dehydrogenation of ethane," J. Mol. Catal. A Chem., vol. 232, no. 1-2, pp. 127-134, May 2005.—incorporated herein by reference in its entirety].

Another way to improve catalyst performance is the addition of promoters. Metal promoters isolate active species and can form secondary metal oxides on support surfaces. For example, molybdenum (Mo) based catalysts were examined with the addition of vanadium and phosphorous. It was observed that vanadium and phosphorous increase catalyst efficiency [N. Haddad, E. Bordes-Richard, L. Hilaire, and a. Barama, "Oxidative dehydrogenation of ethane to ethene on alumina-supported molybdenum-based catalysts modified by vanadium and phosphorus," Catal. Today, vol. 126, no. 1-2, pp. 256-263, August 2007.—incorporated herein by reference in its entirety]. Chromium (Cr) containing oxide pillared zirconium phosphate was synthesized using the fluoro-complex method, and the catalyst was found to be active in oxidative dehydrogenation reactions due to the presence of Cr oxide [B. Solsona, J. M. López-Nieto, M. Alcántara-Rodríguez, E. Rodríguez-Castellón, and a. Jiménez-López, "Oxidative dehydrogenation of ethane on Cr, mixed Al/Cr and mixed Ga/Cr oxide pillared zirconium phosphate materials," J. Mol. Catal. A Chem., vol. 153, no. 1-2, pp. 199-207, March 2000.—incorporated herein by reference in its entirety]. A novel catalyst of $BaCl_2$—$TiO_2$—$SnO_2$ has also been developed [Z. Wang, L. Chen, G. Zou, X. Luo, R. Gao, L. Chou, and X. Wang, "A novel $BaCl_2$—$TiO_2$—$SnO_2$ catalyst for the oxidative dehydrogenation of ethane," Catal. Commun., vol. 25, no. 3, pp. 45-49, August 2012.—incorporated herein by reference in its entirety], and interestingly this catalyst at 720° C. gave very high selectivity for ethylene, and most importantly the $CO_x$ selectivity was very low (7%). For this catalyst, $Cl^-$ ions in the catalyst play a vital and positive role in the oxidative dehydrogenation reaction. Although the catalyst $BaCl_2$—$TiO_2$—$SnO_2$ has deactivation difficulties, the promising result of 60.4% ethylene yield and 92.6% ethylene selectivity made it a promising alternative for ethylene synthesis using a low cost feedstock such as ethane. Lanthanum (La), neodymium (Nd), samarium (Sm) and gadolinium (Gd) based catalysts have been synthesized by modified Sol-gel methods [Q. Zhou, D. Zhou, Y. Wu, and T. Wu, "Oxidative dehydrogenation of ethane over RE-NiO (RE=La, Nd, Sm, Gd) catalysts," J. Rare Earths, vol. 31, no. 7, pp. 669-673, July 2013.—incorporated herein by reference in its entirety]. Gd—NiO showed the best catalytic performance for oxidative dehydrogenation reactions, with 56% ethane conversion and 51% ethylene selectivity at 375° C. Cobalt-titania catalysts were also investigated with the addition of phosphorous [Y. Brik, "Titania-Supported Cobalt and Cobalt-Phosphorus Catalysts: Characterization and Performances in Ethane Oxidative Dehydrogenation," J. Catal., vol. 202, no. 1, pp. 118-128, August 2001.—incorporated herein by reference in its entirety]. The activity of cobalt-titania (anatase) catalysts in oxidative dehydrogenation of ethane was maximal when 7.6 wt % of cobalt was added.

Y-zeolites were treated with transition metals (Ni, Cu and Fe) and then employed in the oxidative dehydrogenation reaction [X. Lin, C. a. Hoel, W. M. H. Sachtler, K. R. Poeppelmeier, and E. Weitz, "Oxidative dehydrogenation (ODH) of ethane with O2 as oxidant on selected transition metal-loaded zeolites," J. Catal., vol. 265, no. 1, pp. 54-62, July 2009.—incorporated herein by reference in its entirety]. It was reported that catalyst activity and $C_2H_4$ selectivity depend on the active metal and follows the trend of Ni>Cu>Fe. In addition, when these metals were used without support, it is reported that they gave selectivity in the range of 50% to 60% at 600 K [Y. Schuurman, V. Ducarme, T. Chen, W. Li, C. Mirodatos, and G. A. Martin, "Low temperature oxidative dehydrogenation of ethane over catalysts based on group VIII metals," Appl. Catal. A Gen., vol. 163, no. 1-2, pp. 227-235, December 1997.—incorporated herein by reference in its entirety].

Lithium (Li), magnesium (Mg), aluminum (Al), gallium (Ga), titanium (Ti), niobium (Nb), and tantalum (Ta) have also been used to enhance the properties of Ni-based mixed metal oxides [Y. Wu, J. Gao, Y. He, and T. Wu, "Preparation and characterization of Ni—Zr—O nanoparticles and its catalytic behavior for ethane oxidative dehydrogenation," Appl. Surf. Sci., vol. 258, no. 11, pp. 4922-4928, March 2012.—incorporated herein by reference in its entirety]. Furthermore, NiO and Nb—NiO nanocomposites have been prepared based on the slow oxidation of a nickel riche Nb—Ni gel obtained in citric acid [H. Zhu, S. Ould-Chikh, D. H. Anjum, M. Sun, G. Biausque, J.-M. Basset, and V. Caps, "Nb effect in the nickel oxide-catalyzed low-temperature oxidative dehydrogenation of ethane," J. Catal., vol. 285, no. 1, pp. 292-303, January 2012.—incorporated herein by reference in its entirety]. The resulting materials have higher surface areas than those obtained by those obtained by the classical evaporation method from nickel nitrate and ammonium niobium oxalate.

Additional work has also been done on nanosized catalysts, specifically a Ni—Zr—O mixture which is prepared by a sol-gel method. Vanadium and phosphorous have also been considered as promoters to enhance the performance in terms of conversion stability and selectivity, but it was found to be less effective than in the molybdenum (Mo) based catalyst [N. Haddad, E. Bordes-Richard, and a. Barama, "MoOx-based catalysts for the oxidative dehydrogenation (ODH) of ethane to ethylene," Catal. Today, vol. 142, no. 3-4, pp. 215-219, April 2009.—incorporated herein by reference in its entirety]. $V_2O_5/Nb_2O_5$ catalysts with various $N_2O_5$ contents were also studied [A. Qiao, V. N. Kalevaru, J. Radnik, a. Srihari Kumar, N. Lingaiah, P. S. Sai Prasad, and a. Martin, "Oxidative dehydrogenation of ethane to ethylene over $V_2O_5/Nb_2O_5$ catalysts," Catal. Commun., vol. 30, pp. 45-50, January 2013.—incorporated herein by reference in its entirety]. The ethylene sensitivity obtained is 38% with a corresponding 28% yield. The activity of the catalyst was related to vanadium (V) species formed, but the low activity presented was attributed to the very low yield of pure $Nb_2O_5$, which is 4%. $MoO_3$—$V_2O_5/Al_2O_3$ is also an effective catalyst in ethane dehydrogenation; however, molybdenum (Mo) addition in this case enhanced catalyst performance by the formation of Mo—V mixed oxides [A. Sri Hari Kumar, K. Upendar, a. Qiao, P. S. N. Rao, N. Lingaiah, V. N. Kalevaru, a. Martin, C. Sailu, and P. S. Sai Prasad, "Selective oxidative dehydrogenation of ethane over MoO3/V2O5-Al2O3 catalysts: Heteropolymolybdate as a precursor for MoO3," Catal. Commun., vol. 33, pp. 76-79, 2013.—incorporated herein by reference in its entirety]. MoVTeNbO was also tested for ethane oxidative dehydrogenation, with the catalyst prepared using a slurry method which was started by silica addition. It was reported that the addition of silica and the synthesis method improved catalyst structure and ultimately the efficiency [T. T. Nguyen, L. Burel, D. L. Nguyen, C. Pham-Huu, and J. M. M. Millet, "Catalytic performance of MoVTeNbO catalyst supported on SiC foam in oxidative dehydrogenation of ethane and ammoxidation of propane," Appl. Catal. A Gen., vol. 433-434, pp. 41-48, 2012.—incorporated herein by reference in its entirety]. The synthesis method also had a great effect on catalyst structure and performance. It was reported that $MoVNbTeO_x$ catalyst gave good results after it was post treated with oxalic acid, which improved the catalyst surface area, and therefor catalyst selectivity and conversion were increased up to 85% and 73% respectively [B. Chu, L. Truter, T. A. Nijhuis, and Y. Cheng, "Applied Catalysis A: General Performance of phase-pure M1 MoVNbTeOx catalysts by hydrothermal synthesis with different post-treatments for the oxidative dehydrogenation of ethane," "Applied Catal. A, Gen., vol. 498, pp. 99-106, 2015.—incorporated herein by reference in its entirety].

Reactor type can also affect the oxidative dehydrogenation reaction and different reactor types such as a fluidized bed membrane reactor and a multi-tubular fixed-bed reactor have been utilized for oxidative dehydrogenation [D. Ahchieva, M. Peglow, S. Heinrich, L. Mörl, T. Wolff, and F. Klose, "Oxidative dehydrogenation of ethane in a fluidized bed membrane reactor," Appl. Catal. A Gen., vol. 296, no. 2, pp. 176-185, December 2005; and E. López, E. Heracleous, A. a. Lemonidou, and D. O. Borio, "Study of a multitubular fixed-bed reactor for ethylene production via ethane oxidative dehydrogenation," Chem. Eng. J., vol. 145, no. 2, pp. 308-315, December 2008.—each incorporated herein by reference in its entirety]. However, only a few studies have reported good ethylene selectivity using these reactors. Furthermore, in the majority of literature, oxygen ($O_2$) was introduced as a gas phase reactant, which can increase feed combustion and lower ethylene selectivity.

An oxygen free environment has been employed to study the ethane oxidative dehydrogenation reaction in fluidized bed reactor conditions (FIG. 1) using 10% VOx supported on c-$Al_2O_3$[S. Al-Ghamdi, M. Volpe, M. M. Hossain, and H. de Lasa, "VOx/c-Al2O3 catalyst for oxidative dehydrogenation of ethane to ethylene: Desorption kinetics and catalytic activity," Appl. Catal. A Gen., vol. 450, pp. 120-130, January 2013.—incorporated herein by reference in its entirety]. Reactivity tests showed that the prepared oxidative dehydrogenation catalyst displayed 6.5-27.6% ethane conversion and 57.6-84.5% ethylene selectivity in the 550-600° C. range. Moderate metal-support interaction and good $VO_x$ dispersion was credited as the key to achieving this desired catalytic performance. In another study, molybdenum (Mo) was introduced to a $VO_x/Al_2O_3$ catalyst, which further enhanced catalyst performance by the formation of $MoO_x$ as secondary surface oxides [I. A. Bakare, S. A. Mohamed, S. Al-Ghamdi, S. A. Razzak, M. M. Hossain, and H. I. de Lasa, "Fluidized bed ODH of ethane to ethylene over VOx-MoOx/ γ-Al2O3 catalyst: Desorption kinetics and catalytic activity," *Chem. Eng. J.*, 2014.—incorporated herein by reference in its entirety].

In view of the forgoing, one object of the present disclosure is to provide novel dehydrogenation catalysts comprising a $VO_x$ catalyst with niobium (Nb) as a promoter to improve $VO_x$ isolation on a support surface of alumina ($Al_2O_3$) modified with lanthanum (La) to minimize the possibility of high temperature alumina phase transition and to afford better thermal stability of the catalyst. A further aim of the present disclosure is to provide a method for producing these multicomponent $VO_x$—Nb/La—$Al_2O_3$ catalysts. An additional aim of the present disclosure is to provide a method for the oxidative dehydrogenation of an alkane to a corresponding olefin employing these multicomponent $VO_x$—Nb/La—$Al_2O_3$ catalysts that may be performed in a gas phase oxygen free environment under circulating fluidized bed reaction conditions while enhancing alkane conversion and alkene selectivity.

BRIEF SUMMARY OF THE INVENTION

According to a first aspect, the present disclosure relates to a dehydrogenation catalyst comprising i) a support material comprising alumina modified by lanthanum and ii) a catalytic material disposed on the support material, wherein the catalytic material comprises one or more vanadium oxides and niobium as a promoter and wherein the dehydrogenation catalyst comprises 10-20% of the one or more vanadium oxides by weight relative to the total weight of the dehydrogenation catalyst.

In one embodiment, the dehydrogenation catalyst comprises 1-5% of niobium by weight relative to the total weight of the dehydrogenation catalyst.

In one embodiment, the dehydrogenation catalyst comprises 0.1-3% of lanthanum by weight relative to the total weight of the dehydrogenation catalyst.

In one embodiment, the dehydrogenation catalyst comprises 30-50% of alumina by weight relative to the total weight of the dehydrogenation catalyst.

In one embodiment, the one or more vanadium oxides have the general formula of $V_nO_{2n+1}$, the general formula of $V_nO_{2n-1}$, or both, wherein n is a whole number greater than zero.

In one embodiment, the one or more vanadium oxides are at least one selected from the group consisting of $V_2O_5$, $VO_2$, and $V_2O_3$.

In one embodiment, the dehydrogenation catalyst comprises at least 50% of $V_2O_5$ by weight relative to the total weight of the one or more vanadium oxides.

In one embodiment, the one or more vanadium oxides form a crystalline phase on the surface of the support material.

In one embodiment, the dehydrogenation catalyst has a BET surface area in the range of 10-50 $m^2/g$.

In one embodiment, the dehydrogenation catalyst has an average particle size in the range of 30-150 m.

In one embodiment, the dehydrogenation catalyst has an apparent particle density in the range of 1-5 $g/cm^3$.

In one embodiment, the dehydrogenation catalyst has a total acidity in the range of 6-11 mL of $NH_3$ per gram of catalyst.

In one embodiment, the dehydrogenation catalyst is fluidizable and has Class B powder properties in accordance with Geldart particle classification.

According to a second aspect, the present disclosure relates to a method for producing the dehydrogenation catalyst of the present disclosure, in one or more of its embodiments, comprising i) mixing lanthanum with alumina to form the support material comprising alumina modified by lanthanum, ii) mixing the support material with a solution comprising a vanadyl salt and a niobium salt in a solvent to form loaded catalyst precursors, iii) reducing the loaded catalyst precursors with $H_2$ gas to form reduced catalyst precursors, and iv) oxidizing the reduced catalyst precursors with oxygen to form the dehydrogenation catalyst.

According to a third aspect, the present disclosure relates to a method for dehydrogenating an alkane to a corresponding olefin comprising flowing the alkane through a reactor comprising a catalyst chamber loaded with the dehydrogenation catalyst at a temperature in the range of 400-800° C. to form the corresponding olefin and a reduced catalyst.

In one embodiment, the reactor is a fluidized bed reactor and the dehydrogenating is performed in an oxygen free environment.

In one embodiment, the method further comprises i) oxidizing the reduced catalyst in an oxygen environment separated from the catalyst chamber to regenerate the dehydrogenation catalyst and ii) repeating the flowing and the oxidizing at least once without a loss in percent conversion of the alkane, a loss in selectivity for the olefin, or both.

In one embodiment, the dehydrogenation catalyst is present at an amount in the range of 0.01-0.5 g per mL of the alkane.

In one embodiment, the alkane is ethane and the method has an ethane conversion of 5-35% at a reaction time of 5-60 seconds and a temperature of 500-600° C.

In one embodiment, the alkane is ethane and the method has an ethylene selectivity of 60-90% at a reaction time of 5-60 seconds and a temperature of 500-600° C.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
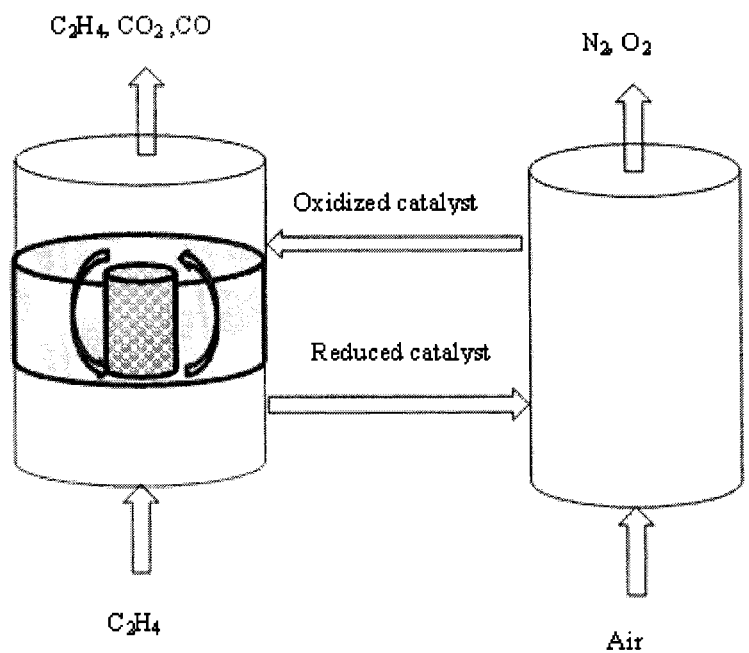
FIG. 1 is a schematic diagram of the fluidized-bed oxidative dehydrogenation process.

Referring now to the drawings, wherein, like reference numerals designate identical or corresponding parts throughout the several views.

According to a first aspect, the present disclosure relates to a dehydrogenation catalyst, comprising i) a lanthanum modified alumina support material, and ii) a catalytic material disposed on the support material, wherein the catalytic material comprises one or more vanadium oxides and niobium as a promoter.

Vanadium oxide is considered to be one of the most important and useful metals to be used as a catalyst due to its physical and chemical properties, and catalysis is the most dominant non-metallurgical use of vanadia. The catalytic activity of vanadia is attributed to its reducible nature and its ability to easily change its oxidation state from $V^{+3}$ to $V^{+5}$. It is generally accepted that $V^{+5}$ is the highly active initial state of the catalyst in a cycle of oxidative dehydrogenation. Vanadium oxide catalysts have been used in many industrial and lab scale catalytic reactions and processes. In many cases, vanadia catalysts are doped with promoters to improve their activity or selectivity, while various supports are used to improve mechanical strength, thermal stability, longevity, and/or catalytic performance.

As used herein, a catalyst support material refers to material, usually a solid with a high surface area, to which a catalyst is affixed. The reactivity of heterogeneous catalyst and nanomaterial based catalysts occurs at the surface atoms. Thus, great effort is made herein to maximize the surface of a catalyst by distributing it over the support. The support may be inert or participate in the catalytic reactions. The support materials used in catalyst preparation play a role in determining the physical characteristics and performance of the catalysts. Typical supports include various kinds of carbon, alumina and silica. In a preferred embodiment, the dehydrogenation catalyst of the present disclosure comprises an alumina support material, preferably a lanthanum modified alumina support material.

As used herein, alumina refers to aluminum oxide, a chemical compound of aluminum and oxygen with the chemical formula Al$_2$O$_3$. Aluminum oxide is commonly called alumina and may also be referred to as aloxide, aloxite, or alundum. It is the most commonly occurring of several aluminum oxides and specifically identified as aluminum (III) oxide. It commonly occurs in its crystalline polymorphic phase α-Al$_2$O$_3$ which composes the mineral corundum, the most thermodynamically stable form of aluminum oxide. Al$_2$O$_3$ is significant in its use to produce aluminum metals and noted for its high melting point. In one embodiment, the catalytic material is loaded on an inert alumina support. Exemplary inert alumina based inert materials include, but are not limited to aluminum oxide, alumina, alumina monohydrate, alumina trihydrate, alumina silica, bauxite, calcined aluminum hydroxides such as gibbsite, bayerite and boehmite as well as calcined hydrotalcite and the like.

In one embodiment, the alumina support material may be comprised of a plurality of different crystallographic phases. In the most common and thermodynamically stable form, corundum, the oxygen ions nearly form a hexagonal close-packed structure with aluminum ions filling two-thirds of the octahedral interstices. Each $Al^{3+}$ center is octahedral. In term of its crystallography, corundum adopts a trigonal Bravais lattice and its primitive cell contains two formula units of aluminum oxide. Aluminum oxide also exists in other phases, including the transition cubic γ and η phases, the monoclinic θ phase, the hexagonal χ phase, the orthorhombic κ phase and the transition δ phase that can be tetragonal or orthorhombic. Each has unique crystal structure and properties. In the present disclosure, aluminum oxide may refer to Al$_2$O$_3$ having an α polymorph, a γ polymorph, a η polymorph, a θ polymorph, a χ polymorph, a κ polymorph and a δ polymorph or mixtures thereof, preferably a γ polymorph. In at least one embodiment, the support material consists essentially of γ-alumina (γ-Al$_2$O$_3$).

Alumina, especially γ-Al$_2$O$_3$ is used for its very high surface area on which active metal atoms/crystallites can spread out as reactive sites, but also for its enhancement of productivity and/or selectivity through metal-support interaction and spillover/reverse-spillover phenomena. In reactions, γ-Al$_2$O$_3$ must retain as much of its high surface area during the reaction. Additives and/or modifiers markedly increase the thermal stability of the support and prevent the loss of surface area under reaction conditions. When lanthanum is used as an additive, the formation of lanthanum aluminate can decrease the surface energies of γ-Al$_2$O$_3$ lowering the driving force for sintering and stabilizing bulk phase transformation of γ-Al$_2$O$_3$. In a preferred embodiment, the dehydrogenation catalyst of the present disclosure comprises an alumina support material, preferably a lanthanum modified alumina support material to stabilize γ-Al$_2$O$_3$.

In a preferred embodiment, the dehydrogenation catalyst of the present disclosure comprises 30-50% of alumina by weight relative to the total weight of the dehydrogenation catalyst, preferably 32-48%, preferably 34-44%, preferably 36-42% of alumina by weight relative to the total weight of the dehydrogenation catalyst. In a preferred embodiment, the dehydrogenation catalyst of the present disclosure comprises 0.1-3.0% of lanthanum by weight relative to the total weight of the dehydrogenation catalyst, preferably 0.5-2.0%, preferably 0.75-1.5%, preferably 0.8-1.1%, or about 1.0% of lanthanum by weight relative to the total weight of the dehydrogenation catalyst.

It is equally envisaged that the dehydrogenation catalyst of the present disclosure may be adapted to incorporate additional support materials and additional additives such as phase transformation stabilizers. In some embodiments, these additional support materials and additional additives may be used in addition to, or in lieu of alumina and/or lanthanum. Exemplary additional support materials include, but are not limited to, $SiO_2$, $TiO_2$, $ZrO_2$, $CeO$, $NbO_5$, $MgO$ and zeolites. Exemplary additional thermal stabilizer additives include, but are not limited to, the elements Ce, Ba, Sr, Sm, Si, Pr and P.

In a preferred embodiment, the dehydrogenation catalyst of the present disclosure comprises a catalytic material disposed on the support material, wherein the catalytic material comprises one or more vanadium oxides and niobium as a promoter. As used herein, "disposed on" or "impregnated" describes being completely or partially filled throughout, saturated, permeated and/or infused. The catalytic material may be affixed on one or more surfaces of the support material the catalytic material may be affixed on an outer surface of the support material or within pore spaces of the support material. The catalytic material may be affixed to the support material in any reasonable manner, such as physisorption or chemisorption and mixtures thereof. In one embodiment, greater than 10% of the surface area (i.e. surface and pore spaces) of the support material is covered by the catalytic material, preferably greater than 15%, preferably greater than 20%, preferably greater than 25%, preferably greater than 30%, preferably greater than 35%, preferably greater than 40%, preferably greater than 45%, preferably greater than 50%, preferably greater than 55%, preferably greater than 60%, preferably greater than 65%, preferably greater than 70%, preferably greater than 75%, preferably greater than 80%, preferably greater than 85%, preferably greater than 90%, preferably greater than 95%, preferably greater than 96%, preferably greater than 97%, preferably greater than 98%, preferably greater than 99%.

In a preferred embodiment, the catalytic material comprises one or more vanadium oxides and niobium as a promoter. In terms of the present disclosure, vanadium oxide may refer to vanadium (II) oxide (vanadium monoxide, VO), vanadium (III) oxide (vanadium sesquioxide or trioxide, $V_2O_3$), vanadium (IV) oxide (vanadium dioxide, $VO_2$), vanadium (V) oxide (vanadium pentoxide, $V_2O_5$). Vanadium oxide may also refer to a vanadate, a compound containing on oxoanion of vanadium generally in its highest oxidation state of $^+5$. The simplest vanadate ion is the tetrahedral orthovanadate $VO_4^{3-}$ anion. Exemplary vanadate ions include, but are not limited to, $VO_4^{3-}$, $V_2O_7^{4-}$, $V_3O_9^{3-}$, $V_4O_{12}^{4-}$, $V_5O_{14}^{3-}$ and the like. In addition to these principal oxides of vanadium, various other distinct phases exist. Phases with the general formula $V_nO_{2n+1}$, wherein n is a whole number greater than zero exist between $V_2O_5$ (vanadium (V) species) and vanadium (IV) species. Examples of these phases include $V_3O_7$, $V_4O_9$ and $V_6O_{13}$. Phases with the general formula $V_nO_{2n-1}$, wherein n is a whole number greater than zero exist between vanadium (IV) species and $V_2O_3$ (vanadium (III) species). Termed Magneli phases, they are examples of crystallographic shear compounds based on rutile structure. Examples of Magneli phases include $V_4O_7$, $V_5O_9$, $V_6O_{11}$, $V_7O_{13}$ and $V_8O_{15}$. Many vanadium oxygen phases are non-stoichiometric. In a preferred embodiment, the dehydrogenation catalyst of the present disclosure comprises 10-20% of the one or more vanadium oxides by weight relative to the total weight of the dehydrogenation catalyst, preferably 11-18%, preferably 12-16%, preferably 13-15% of the one or more vanadium oxides by weight relative to the total weight of the dehydrogenation catalyst.

In a preferred embodiment, the one or more vanadium oxides are of the formula $V_xO_y$, wherein x=1-4, preferably 1-3, more preferably 1-2 and y=2-10, preferably 2-5. In a preferred embodiment, the one or more vanadium oxides are at least one selected from the group consisting of $V_2O_5$, $VO_2$ and $V_2O_3$. $V_2O_5$ or vanadium (V) oxide or vanadium pentoxide is an inorganic compound that due to its high oxidation state is both an amphoteric oxide and an oxidizing agent. $V_2O_5$ is characterized by its valuable redox properties as $V_2O_5$ is easily reduced to the stable vanadium (IV) species. In certain embodiments, the dehydrogenation catalyst comprises at least 50% of $V_2O_5$ by weight relative to the total weight of the one or more vanadium oxides, preferably greater than 60%, preferably greater than 70%, preferably greater than 80%, preferably greater than 85%, preferably greater than 90%, preferably greater than 95%, preferably greater than 96%, preferably greater than 97%, preferably greater than 98%, preferably greater than 99% of $V_2O_5$ by weigh relative to the total weight of the one or more vanadium oxides, such as, for example 50-90% by weight $V_2O_5$, preferably 75-80% $V_2O_5$, more preferably 85-90% $V_2O_5$, even more preferably at least 90-95% $V_2O_5$, most preferably 95-99.9% $V_2O_5$ relative to the total weight of the one or more vanadium oxides. In some embodiments, the dehydrogenation catalyst of the present disclosure consists essentially of $V_2O_5$ and is substantially free of $V_2O_3$ and $VO_2$. In some embodiments, the dehydrogenation catalyst of the present disclosure is substantially free of $V_2O_3$ and comprises a mixture of at least 50% $V_2O_5$ by weight relative to the total weight of the one or more vanadium oxides, with the balance substantially comprising $VO_2$.

The different vanadia phases that can be present in supported vanadia oxide catalysts as well as the distribution among the various vanadium oxide structures can depend on the synthesis method, the vanadium precursor, solvent, calcination temperature, vanadium oxide loading, oxide support, etc. At loadings below "monolayer coverage" isolated and oligomerized surface $VO_4$ species may be present on the oxide support. The surface $VO_4$ species may possess up to three different oxygen atoms including, but not limited to, oxygen atoms forming a vanadyl group (V=O), oxygen atoms bridging two vanadia atoms (V—O—V), and oxygen atoms bridging a vanadia atom and oxide support cation (V—O-support). Depending on the vanadia surface density as well as the support material, a vanadia "monolayer coverage" may be reached. A "monolayer" refers to a single, closely packed layer of atoms or molecules, here the one or more vanadium oxides. As used herein, "monolayer coverage" refers to the completion of a 2D surface of vanadium oxide overlayer on the alumina support, and the surface becomes saturated before 3D vanadium oxide and/or $V_2O_5$ crystallites start to form and grow. Alternatively, the monolayer coverage may be thought of as the minimum amount of single vanadium and/or vanadium oxide atoms or molecules to cover exactly 100% of the surface area (surface and pore spaces) of the catalyst support material uniformly. In a preferred embodiment, the monolayer coverage of the dehydrogenation catalyst of the present disclosure corresponds to 5-20 vanadium atoms per $nm^2$ of support, preferably 6-15 atoms/$nm^2$, preferably 7-10 atoms/$nm^2$, preferably 8-9 vanadium atoms per $nm^2$ of support. In certain embodiments, $V_2O_5$ crystallites may be present at vanadium oxide loadings below monolayer coverage when a precursor vanadium salt is not well dispersed over the support during synthesis or when a weak interaction exists between the vanadium oxide and the support. In one embodiment, the one or more vanadium oxides may form a crystalline phase on the surface of the lanthanum modified alumina support material, preferably a $V_2O_5$ crystalline phase. At high enough loadings, greater than monolayer coverage, vanadium oxide nanocrystals or nanoparticles having an average particle size of 1-100 nm, preferably 4-80 nm, preferably 10-60 nm, preferably 20-40 nm may be present on the surface of the catalyst support. In certain embodiments, the different surface vanadia species may be identified by techniques including, but not limited to, Raman spectroscopy, UV-vis spectroscopy, X-ray powder diffraction (XRD) and the like. For example, as evaluated by XRD, the catalytic material comprising one or more vanadium oxides of the present disclosure forms a crystalline phase on the support surface. In other embodiments, the catalytic material may display an amorphous phase.

In a preferred embodiment, the catalytic material comprises one or more vanadium oxides and niobium as a promoter. As used herein, a promoter refers to an additive to improve catalyst performance. Metal promoters may function to isolate active species (i.e. $VO_x$, more preferably $V_2O_5$) and to form secondary metallic oxides (i.e. $Nb_2O_5$) on support surface. Furthermore, the addition of promoters to the catalytic material blocks acid sites which decreases the total acidity of the dehydrogenation catalyst. In certain embodiments, the decrease in acidity and increase in basicity may facilitate desorption of substrates from the dehydrogenation catalyst surface, preventing further oxidation, such as, for example the undesirable combustion to carbon oxides ($CO_x$) in the oxidative dehydrogenation of light alkanes such as ethane and propane. In a preferred embodiment, the dehydrogenation catalyst of the present disclosure comprises 1.0-5.0% of niobium by weight relative to the total weight of the dehydrogenation catalyst, preferably 1.5-4.0%, preferably 2.0-3.75%, preferably 3.0-3.5%, or about 3.25% of niobium by weight relative to the total weight of the dehydrogenation catalyst. It is equally envisaged that the dehydrogenation catalyst of the present disclosure may be adapted to incorporate additional promoters. In some embodiments, these additional promoters may be used in addition to, or in lieu of niobium. Exemplary additional promoters include, but are not limited to, metallic promoters (Cr, Mo, Ta, W), alkali promoters (Li, K, Rb) and halide promoters (Cl). In preferred embodiments, the vanadium and niobium are homogeneously distributed throughout the catalyst support. In other embodiments the niobium may form localized clusters amongst the vanadium, form niobium oxide species with the support catalyst, or be disposed on the vanadium oxide species and mixtures thereof.

In a preferred embodiment, the present disclosure provides fluidizable dehydrogenation catalysts for oxidative dehydrogenation (ODH) of alkanes preferably in reactors having a fluidized bed design. As used herein "fluidizable" refers to the ability to undergo fluidization which refers to a process similar to liquefaction whereby a granular material is converted from a static solid-like to a dynamic fluid-like state. The process occurs when a fluid (liquid or gas) is passed up through the granular material. A fluidized bed is formed when a quantity of a solid particulate substance is placed under appropriate conditions to cause a solid/fluid mixture to behave as a fluid. This is usually achieved by the introduction of pressurized fluid through the particulate medium. This results in the medium then having many properties and characteristics of normal fluids, such as the ability to free flow under gravity, or to be pumped using fluid type technologies. Fluidized bed types can be broadly classified by their flow behavior including, but not limited to, stationary or bubbling fluidized beds, circulating fluidized beds (CFB), vibratory fluidized beds, transport or flash reactor (FR), and annular fluidized beds (AFB).

In a fluidized bed reactor, the catalyst pellets lie on a grate at the bottom of the reactor. Reactants are continuously bumped into the reactor through a distributor causing the bed to become fluidized. During the fluidization, the catalyst pellets are converted from a static solid like state to a dynamic fluid like state. The bed's behavior after initial fluidization depends on the state of the reactant. If it is a liquid the bed expands uniformly with an increased upward flow of the reactant, resulting in a homogeneous fluidization. If the reactant is a gas, the bed will be non-uniform because the gas forms bubbles in the bed, resulting in aggregative fluidization. In terms of the present disclosure, the fluidization may be homogeneous or aggregative. In certain embodiments, the reactant or feed is preferably a light alkane including, but not limited to, ethane, propane and butane (including n-butane and isobutene), all of which are gases and hence, an aggregative fluidization may be more probable.

Properties and parameters for determining the fluidizability, reducibility, and oxygen carrying capacity of a catalyst can be both measured and calculated. The average particle size and the particle size distribution can be measured, for example, using a Mastersizer 2000 from Malvern Instruments. For spherical or substantially spherical dehydrogenation catalyst particles, average particle size refers to the longest linear diameter of the dehydrogenation catalyst particles. In a preferred embodiment, the dehydrogenation catalyst of the present disclosure in any of its embodiments has an average particle size in the range of 30-150 µm, preferably 40-120 µm, preferably 50-100 µm, more preferably 60-80 µm. In one embodiment, the particle size distribution of the dehydrogenation catalyst of the present disclosure is 10-200 µm and greater than 75% of the particles have a particle size of 40-120 µm, preferably greater than 80%, preferably greater than 85%, more preferably greater than 90% have a particle size of 40-120 µm. In another embodiment, the dehydrogenation catalyst of the present disclosure has a particle size distribution ranging from 33% of the average particle size to 133% of the average particle size, preferably 50-130%, preferably 60-125%, preferably 80-100%, preferably 90-110%, preferably 95-105% of the average particle size. In one embodiment, the dehydrogenation catalyst particles of the present disclosure are monodisperse, having a coefficient of variation or relative standard deviation, expressed as a percentage and defines as the ratio of the particle size standard deviation ($\sigma$) to the particle mean size ($\mu$) multiplied by 100 of less than 25%, preferably less than 20%, preferably less than 15%, preferably less than 12%, preferably less than 10%, preferably less than 8%, preferably less than 6%, preferably less than 5%.

As used herein, the apparent particle density refers to the mass of the catalyst divided by the volume that it occupies. The apparent particle density can be assessed using a CREC-established method. In the method, a known amount of catalyst is introduced to a flask. The flask is filled with isopropanol and the apparent particle density (AD) is calculated using the following equation, formula (I).

$$AD = \frac{W_{cat}}{V_T - V_{isopropanol}} \quad (I)$$

Where AD is the apparent particle density (g/cm$^3$), $W_{cat}$ is the catalyst weight, $V_T$ is the flask volume and $V_{isopropanol}$ is the volume of isopropanol calculated as the ratio of the weight of isopropanol needed to fill the flask and the density of isopropanol. In a preferred embodiment, the dehydrogenation catalyst of the present disclosure in any of its embodiments has an apparent particle density of 1.0-5.0 g/cm$^3$, preferably 1.23-4.0 g/cm$^3$, preferably 1.5-3.5 g/cm$^3$, more preferably 1.8-3.2 g/cm$^3$.

In some embodiments, with the calculated average particle size and particle apparent density values, the fluidization regime of the dehydrogenation catalyst particles of the present disclosure can be determined using Geldart's powder classification chart. Geldart groups powders into four "Geldart Groups" or "Geldart Classes". The groups are defined by solid-fluid density difference and particle size. Design methods for fluidized beds can be tailored based upon a particle's Geldart Group. For Geldart Group A the particle size is between 20 and 100 µm and the particle density is typically less than 1.4 g/cm$^3$. Prior to the initiation of a bubbling bed phase, beds from these particles will expand by a factor of 2 to 3 at incipient fluidization, due to ta decreased bulk density. Most powder-catalyzed beds utilize this group. For Geldart Group B the particle size lies between 40 and 500 µm and the particle density is between 1.4-4 g/cm$^3$. Bubbling typically forms directly at incipient fluidization. For Geldart Group C the group contains extremely fine and consequently the most cohesive particles. With a particle size of 20 to 30 µm, these particles fluidize under very difficult to achieve conditions, and may require the application of an external force, such as mechanical agitation. For Geldart Group D the particles in this regime are above 600 µm and typically have high particle densities. Fluidization of this group requires very high fluid energies and is typically associated with high levels of abrasion. Additionally, these particles are usually processed in shallow beds or in the spouting mode. The dehydrogenation catalyst of the present disclosure may be classified as a Geldart Group A powder, a Geldart Group B powder, a Geldart Group C powder or a Geldart Group D powder, preferably as a Geldart Group B powder. In at least one preferred embodiment, the dehydrogenation catalyst particles display a Geldart Group B powder property, which is highly fluidizable under ODH conditions. Large particles, such as those under Geldart Group D, may limit the gas phase reactant access to the inner layers of the catalyst. As a result, using smaller particles can minimize the diffusional resistance and reduction/oxidation rates can be maximized. On the other hand, very small particles, such as those under Geldart's Group C, can cause fluidization problems, channeling and loss of fines.

The Brunauer-Emmet-Teller (BET) theory aims to explain the physical adsorption of gas molecules on a solid surface and serves as the basis for an important analysis technique for the measurement of the specific surface area of a material. Specific surface area is a property of solids which is the total surface area of a material per unit of mass, solid or bulk volume, or cross sectional area. In a preferred embodiment, the dehydrogenation catalyst of the present disclosure in any of its embodiments has a BET surface area in the range of 10-50 m$^2$/g, preferably 12-40 m$^2$/g, preferably 14-30 m$^2$/g, preferably 15-25 m$^2$/g, preferably 16-20 m$^2$/g. In one embodiment, the inclusion of niobium (Nb) as a promoter increases the BET surface area of the dehydrogenation catalyst by 10-50% relative to a substantially similar catalyst lacking niobium, preferably 15-40%, preferably 20-35% relative to a substantially similar catalyst lacking niobium. In one embodiment, the dehydrogenation catalyst of the present disclosure possesses a narrow size mesoporosity and a nitrogen monolayer adsorption on the catalyst surface. In one embodiment, the observed nitrogen ($N_2$) monolayer coverage is a good indicator of the catalyst's ability to maintain surface area, and thus $VO_x$ dispersion under reaction conditions. In a preferred embodiment, the dehydrogenation catalyst of the present disclosure has a $N_2$ monolayer volume of 2-8 mL of $N_2$ per gram of catalyst, preferably 3-6 mL/g, preferably 3.5-5.75 mL of $N_2$ per gram of catalyst.

The catalytic activity of many oxides in various processes is due to their Lewis and Bronsted acidities. In addition to the effect on surface area, the niobium modification may also depress the surface acidity and metal-support interactions of the catalyst, thereby enhancing olefin selectivity in oxidative dehydrogenation reactions and reducing coke ($CO_x$) formation. The catalyst acidity plays a role in metal support interactions that affect $VO_x$ reducibility. The reducibility may impact catalyst activity and selectivity by providing $O_2$ for oxidation and high acidity not favoring selective oxidation. A number of techniques have been developed for the characterization of acid-base surface properties of catalysts. The adsorption of volatile amines including, but not limited to, ammonia ($NH_3$), pyridine ($C_5H_5N$), n-butylamine ($CH_3CH_2CH_2CH_2NH_2$), quinolone ($C_9H_7N$) and the like is often used to determine the acid site concentration of solid catalysts. The amount of the base remaining on the surface after evacuation is considered chemisorbed and serves as a measure of the acid site concentration. The adsorbed base concentration as a function of evacuation temperature can give a site strength distribution. Another means of determining the site strength distribution is calorimetry or the temperature-programmed desorption (TPD).

Ammonia or $NH_3$-TPD experiments are used to determine the total acidity of the catalyst. TPD can further give an idea about metal-support interactions by modeling $NH_3$ desorption kinetics and be used to determine the strength of acid sites available on the catalyst surface. In a preferred embodiment, the dehydrogenation catalyst of the present disclosure in any of its embodiments has a total acidity in the range of 6-11 mL of $NH_3$ per gram of catalyst, preferably 7-10 mL of $NH_3$ per gram of catalyst, preferably 7-9.5 mL of $NH_3$ per gram of catalyst, preferably 7-9 mL of $NH_3$ per gram of catalyst, preferably 7.5-8.5 mL of $NH_3$ per gram of catalyst when measured with a heating rate of 5-20° C./min, preferably 10-15° C./min.

In one embodiment, the inclusion of niobium (Nb) as a promoter may decrease the total acidity of the dehydrogenation catalyst, preferably by less than 2.0 mL of $NH_3$ per gram of catalyst, preferably by less than 1.5 mL of $NH_3$ per gram of catalyst, preferably by less than 1.0 mL of $NH_3$ per gram of catalyst, preferably by less than 0.5 mL of $NH_3$ per gram of catalyst when measured with a heating rate of 5-20° C./min, preferably 10-15° C./min. relative to a substantially similar catalyst lacking niobium. In addition, the effects of niobium modification can be established by $NH_3$ desorption kinetic analysis. In a preferred embodiment, the dehydrogenation catalyst of the present disclosure have an energy of $NH_3$ desorption in the range of 50-100 kJ/g, preferably 70-90 kJ/g, preferably 72-85 kJ/g, preferably 75-82 kJ/g. In some embodiments, niobium may decrease the catalyst acidity by covering some acid sites. In a preferred embodiment, the dehydrogenation catalyst of the present disclosure has a lower acidity than pure alumina (~14-15 mL of $NH_3$ per gram of alumina).

According to a second aspect, the present disclosure relates to a method for producing the dehydrogenation catalyst of the present disclosure in any of its embodiments, comprising i) mixing lanthanum with alumina to form the lanthanum modified support material, ii) mixing the lanthanum modified support material with a solution comprising a vanadium salt and a niobium salt in a solvent to form loaded catalyst precursors, iii) reducing the loaded catalyst precursors with $H_2$ gas to form reduced catalyst precursors, and iv) oxidizing the reduced catalyst precursors with oxygen to form the dehydrogenation catalyst.

Two main methods are typically used to prepare supported catalysts. In the impregnation method, the solid support or a suspension of the solid support is treated with a solution of a precatalyst (for instance a metal salt or metal coordination complex), and the resulting material then activated under conditions that will convert the precatalyst to a more active state, such as the metal itself or metal oxides of the metal. In such cases, the catalyst support is usually in the form of pellets or spheres. Alternatively, supported catalysts can be prepared from homogenous solution by co-precipitation. In terms of the present disclosure, it is envisaged that the dehydrogenation catalyst may be formed by an impregnation method or a co-precipitation method, preferably by an impregnation method. Supports are usually thermally very stable and withstand processes required to activate precatalysts. For example, many precatalysts are activated by exposure to a stream of hydrogen or air (oxygen) at high temperatures, additionally many precatalysts may be activated and/or reactivated by oxidation-reduction cycles, again at high temperatures.

In one step of the process, lanthanum is mixed with alumina to form the lanthanum modified support material. In one embodiment, the unmodified alumina may be optionally initially dried and/or calcined to remove moisture and other volatile compounds. The preemptive drying may be performed at a temperature of 300-400° C., preferably 350-400° C., or about 375° C. for a period of up to 6 hours, preferably up to 2 hours, or about 1 hour. The precalcining may be performed at a temperature of 600-800° C., preferably 650-750° C., or about 725° C. for a period of up to 8 hours, preferably up to 6 hours, or about 4 hours. In a preferred embodiment, the lanthanum modified alumina is prepared by an incipient wetness method of impregnation. The alumina support can then be immersed in a solution, preferably an aqueous solution comprising lanthanum and/or a lanthanum salt. Exemplary lanthanum salts include, but are not limited to, lanthanum (III) trifluoromethanesulfonate, lanthanum (III) nitrate hexahydrate, lanthanum (III) acetate hydrate, and the like. In a preferred embodiment the solution has a lanthanum concentration of 0.01-1.0 M, preferably 0.05-0.5 M, preferably 0.1-0.25 M, preferably 0.125-0.2 M, or about 0.15 M. In a preferred embodiment, the weight ratio of alumina to lanthanum in the solution is in the range of 200:1 to 10:1, preferably 150:1 to 50:1, preferably 120:1 to 80:1, or about 100:1. In a preferred embodiment, the mixing of the lanthanum with the alumina is performed at a temperature of 20-40° C., preferably 20-30° C., or about 25° C. for a period of less than 120 minutes, preferably less than 90 minutes, preferably less than 60 minutes, preferably less than 40 minutes, preferably less than 20 minutes and optionally with stirring and/or ultrasonication to achieve a homogeneous mixture. In a preferred embodiment, the soaked/impregnated niobium loaded/modified support material is then dried by calcination at a temperature of up to 600° C., preferably up to 500° C., preferably up to 450° C., preferably up to 400° C. for a time of up to 12 hours, preferably up to 8 hours, preferably up to 6 hours, preferably up to 4 hours.

In one step of the process the lanthanum modified support material is mixed with a solution comprising a vanadyl salt and a niobium salt in a solvent to form loaded catalyst precursors. The manner in which the vanadium oxide is deposited onto a support can have an influence on the properties of the active component in the final catalyst. Typically the main method of dispersing vanadium oxide on support materials is the classic incipient wetness impregnation method in a solvent where the vanadium salt is soluble. The impregnation method is performed by contacting the support with a certain volume of solution containing the dissolved vanadium oxide precursor. If the volume of the solution is either equal to or less than the pore volume of the support, the technique is referred to as incipient wetness. This particular synthesis route can show a broad variation of vanadium oxide surface species at all loadings, particularly loadings below monolayer coverage, depending on the synthesis conditions. In one embodiment, this method may lead to the formation of three-dimensional $V_2O_5$ nanoparticles, even at low vanadium oxide loadings.

In one embodiment, the vanadium salt may be a vanadium (IV), vanadium (V) or vanadium (III) salt. Exemplary vanadium salts include, but are not limited to, ammonium metavanadate in mixtures of water and oxalic acid or methanol and oxalic acid, vanadium (III) acetylacetonate $(V(AcAc)_3)$ or vanadyl acetylacetonate $(VO(AcAc)_2)$ in toluene, $VO(iPrO)_3$, $VO(OC_2H_5)_3$, or $VO(OC_2H_7)_3$ in 2-propanol, as well as vanadyl sulfate, vanadium pentoxide, vanadium oxytripropoxide, tetrakis(diethylamido)vanadium (IV), vanadium (III) chloride, vanadium (IV) chloride, vanadium (III) chloride tetrahydrofuran complex, vanadium (V) oxychloride, vanadium (V) oxyfluoride, and the like. Preferably, the vanadium salt is $V(AcAc)_3$. The vanadium salt is preferably phosphorous free. In one embodiment, the niobium salt may be a niobium (IV), niobium (V) or niobium (III) salt. Exemplary niobium salts include, but are not limited to, niobium (V) chloride, ammonium niobate (V) oxalate hydrate, niobium (III) chloride 1,2-dimethoxyethane complex, niobium (IV) chloride tetrahydrofuran complex, niobium (V) fluoride, and the like. Preferably, the niobium salt is niobium (V) chloride. In a preferred embodiment, the solvent is a non-polar solvent. Exemplary non-polar solvents include, but are not limited to, pentane, cyclopentane, hexane, cyclohexane, benzene, toluene, 1,4-dioxane, chloroform, diethyl ether and dichloromethane, preferably the solvent is toluene. It is equally envisaged that the present method may be adapted to incorporate polar aprotic solvents including, but not limited to, tetrahydrofuran, ethyl acetate, acetone, dimethylformamide, acetonitrile, dimethyl sulfoxide, nitromethane and propylene carbonate as well as polar protic solvents including, but not limited to, formic acid, n-butanol, isopropanol, n-propanol, ethanol, methanol, acetic acid, and water and mixtures thereof.

In a most preferred embodiment the vanadium salt is $V(AcAc)_3$ and the niobium salt is niobium (V) chloride and the solvent is toluene. In a preferred embodiment the solution has a vanadium concentration of 0.01-1.0 M, preferably 0.05-0.5 M, preferably 0.1-0.25 M, preferably 0.125-0.2 M, or about 0.15 M. In a preferred embodiment, the weight ratio of vanadium to niobium in the solution is in the range of 10:1 to 2:1, preferably 8:1 to 3:1, preferably 6:1 to 4:1. In a preferred embodiment, the mixing of the lanthanum modified support material with the solution comprising a vanadium salt and a niobium salt in a solvent is performed at a temperature of 20-40° C., preferably 20-30° C., or about 25° C. for a period of less than 48 hours, preferably less than 36 hours, preferably less than 24 hours, preferably less than 18 hours, preferably less than 12 hours, preferably less than 10 hours and optionally with stirring and/or ultrasonication to achieve a homogeneous mixture. After mixing the solution can be filtered and separated from the solvent to provided loaded catalyst precursors.

In another embodiment, it is equally envisaged that the method may be adapted to other means of dispersing and depositing the vanadium oxide on the support material. Both adsorption from solution (i.e. grafting) based on attaching vanadia from the solution through reaction with hydroxyl groups on the surface of the support and ion exchange methods permitting the ionic vanadium oxide species present in an aqueous solution to be electrostatically attracted by charged sites of the support surface have been used. Exemplary other means include, but are not limited to, vapor-fed flame synthesis, flame spray pyrolysis, sputter deposition, atomic layer deposition and chemical vapor deposition (CVD). For example, chemical vapor deposition (CVD) uses volatile molecular metal precursors (i.e. $O=VCl_3$, $O=V(OC_2H_5)_3$ or $O=V(OiPr)_3$) to modify oxide support surface and provide a way to control the dispersion of the active sites.

In certain embodiments, in addition to the methods employed to disperse vanadium oxide material on different supports, the drying and/or calcination used for the fixation of the vanadia may be a crucial step of the catalyst preparation due to the conversion of the initial vanadium species that may result in a broad variety of $V_xO_y$ species from a nominally simple impregnation process. At high calcination temperatures, mixed oxide compounds or solid solutions can be formed with some oxide supports (i.e. $AlVO_4$). In a preferred embodiment, the loaded catalyst supports are dried before the reduction and the oxidation at a temperature of up to 300° C., preferably up to 250° C., preferably up to 200° C., preferably up to 175° C., preferably up to 150° C. for a period of up to 60 hours, preferably up to 48 hours, preferably up to 36 hours, preferably up to 24 hours, preferably up to 12 hours.

In one step of the process the loaded catalyst precursors are reduced with $H_2$ gas to form reduced catalyst precursors. As used herein, reduction refers to the gain of electrons or a decrease in oxidation state by a molecule, atom or ion. In a preferred embodiment, the loaded catalyst precursors are reduced under a flow of hydrogen gas comprising 50-99% $H_2$, preferably 60-98% $H_2$, preferably 70-96% $H_2$, preferably 80-94% $H_2$, preferably 85-92% $H_2$, or about 90% $H_2$ as a molar percentage and 1-50% inert gas, preferably 2-40% inert gas, preferably 4-30% inert gas, preferably 6-20% inert gas, preferably 8-15% inert gas, or about 10% inert gas as a molar percentage. Exemplary inert gases include nitrogen ($N_2$) and argon (Ar), preferably argon. In a preferred embodiment, the reduction under hydrogen gas flow is performed at a temperature of 400-800° C., preferably 450-750° C., preferably 500-700° C., preferably 525-675° C., preferably 550-650° C., preferably 575-625° C., or about 600° C. for a period of 1-18 hours, preferably 2-12 hours, preferably 4-8 hours, or about 6 hours.

In one step of the process the reduced catalyst precursors are oxidized with oxygen to form the dehydrogenation catalyst of the present disclosure in any of its embodiments. As used herein, oxidation refers to the loss of electrons or an increase in oxidation state by a molecule, atom or ion. Oxidation reactions are commonly associated with the formation of oxides from oxygen molecules. Oxygen itself is the most versatile oxidizer. In a preferred embodiment, the reduced catalyst precursors are oxidized under air flow comprising 20-25% $O_2$, preferably 20.5-22% $O_2$, or about 21% $O_2$ as a molar percentage and 75-80% $N_2$, preferably 77-79% $N_2$, or about 78% $N_2$ as a molar percentage. In a preferred embodiment, the oxidation under air flow is performed at a temperature of 300-700° C., preferably 350-650° C., preferably 400-600° C., preferably 425-575° C., preferably 450-550° C., preferably 475-525° C., or about 500° C. for a period of time of 1-12 hours, preferably 2-8 hours, preferably 4-6 hours, or about 5 hours.

According to a third aspect, the present disclosure relates to a method for dehydrogenating an alkane to a corresponding olefin comprising flowing the alkane through a reactor comprising a catalyst chamber loaded with the dehydrogenation catalyst of the present disclosure in any of its embodiments at a temperature in the range of 400-800° C. to form the corresponding olefin and a reduced catalyst.

The general nature of the alkane substrate is not viewed as particularly limiting to the oxidative dehydrogenation described herein. As used herein, "alkane" or "paraffin" unless otherwise specified refers to both branched and straight chain saturated primary, secondary and/or tertiary hydrocarbons of typically $C_1$-$C_{10}$. It is equally envisaged that the present disclosure may be adapted to cycloalkanes referring to cyclized alkanes containing one or more rings and substituted alkanes and/or substituted cycloalkanes referring to at least one hydrogen atom that is replaced with a non-hydrogen group, provided that normal valencies are maintained and that the substitution results in a stable compound. In a preferred embodiment, the alkane is at least one straight-chain linear alkane of $C_1$ to $C_{10}$, preferably $C_2$-$C_6$, more preferably $C_2$-$C_4$ selected from the group consisting of ethane ($C_2H_6$), propane ($C_3H_8$), and a butane ($C_4H_{10}$, n-butane, isobutane) and the corresponding olefin is a light olefin selected from the group consisting of ethylene, propylene, a butene (1-butene, (Z)-but-2-ene, (E)-but-2-ene, isobutylene (2-methylpropene)) and butadiene respectively, more preferably the alkane is ethane or propane and the corresponding olefin is ethylene or propylene respectively, most preferably ethane and ethylene. In certain embodiments, the alkane may be sourced from other industrial processes such as those used in the petrochemical industry. Feedstocks generated from petroleum including, but not limited to, ethane, propane, butane, naphtha, pet naphtha, pygas, light pygas, and gas oil may serve as substrates for the method of dehydrogenating an alkane described herein. In some embodiments, these streams or feedstocks may be processed (i.e. hydroprocessed) prior to the dehydrogenation.

As used herein, dehydrogenation refers to a chemical reaction that involves the removal of hydrogen from a molecule. It is the reverse process of hydrogenation. The dehydrogenation reaction may be conducted on both industrial and laboratory scales. Essentially dehydrogenation converts saturated materials to unsaturated materials and dehydrogenation processes are used extensively in fine chemicals, oleochemicals, petrochemicals and detergents industries. The most relevant industrial pathway in light olefin production is typically steam cracking and fluid catalytic cracking is only able to produce desired olefins in small concentrations with significant catalyst deactivation. The catalytic dehydrogenation of alkanes is more selective but the reaction characteristics pose inherent difficulties and impose certain technical constraints. For example, thermal dehydrogenation is strongly endothermic and often requires operation at both high temperature and high alkane partial pressure. The oxidative dehydrogenation (ODH) of an alkane, which couples the endothermic dehydrogenation of the alkane with the strongly exothermic oxidation of hydrogen avoids the need for excess internal heat input and consumes hydrogen. The advantages of the alkane ODH reaction include that the reaction is i) exothermic, ii) thermodynamically unrestricted, iii) operates at a much lower temperature, and iv) minimizes coke ($CO_x$) deposition ensuring long-term stability of the catalyst.

Under standard operating conditions, an alkane is converted to a corresponding olefin by oxidative dehydrogenation in the presence of the dehydrogenation catalyst described herein in accordance with the chemical equation represented by formula (II), wherein y is a positive whole number, preferably y is 2, 3, or 4, more preferably y is 2 and the alkane converted is ethane and the corresponding olefin is ethylene.

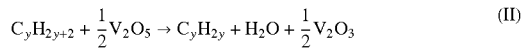

$$C_yH_{2y+2} + \frac{1}{2}V_2O_5 \rightarrow C_yH_{2y} + H_2O + \frac{1}{2}V_2O_3 \quad (II)$$

In some embodiments the alkane to olefin conversion may be accompanied by complete oxidation of the alkane or the olefin as side and/or secondary reactions as represented in formula (III) and formula (IV), wherein y is a positive whole number, preferably y is 2, 3, or 4, more preferably y is 2, and y is the sum of a and b (y=a+b). The yield of alkenes or olefins obtained by oxidative dehydrogenation on catalysts is limited by alkene or alkane combustion to $CO_x$ (i.e. CO and $CO_2$). The minimization of these undesirable consecutive and/or parallel combustion reactions is a key in the development of successful oxidative dehydrogenation catalysts.

$$C_yH_{2y+2} + \frac{1}{2}V_2O_5 \rightarrow aCO_2 + bCO + \frac{(2y-2)}{2}H_2O + \frac{1}{2}V_2O_3 \quad (III)$$

$$C_yH_{2y} + \frac{1}{2}V_2O_5 \rightarrow aCO_2 + bCO + \frac{2y}{2}H_2O + \frac{1}{2}V_2O_3 \quad (IV)$$

The performance of the oxidative dehydrogenation can be modulated by adjusting conditions including, but not limited to, temperature, pressure, reaction time and/or catalyst loading. One important objective in developing oxidative dehydrogenation catalysts is to reduce the reaction temperature of the process to minimize energy consumption. In a preferred embodiment, the oxidative dehydrogenation of an alkane to a corresponding olefin is carried out a temperature in the range of 400-800° C., preferably 450-750° C., preferably 500-700° C., preferably 525-675° C., preferably 550-625° C., preferably 575-600° C. and preferably at standard pressure (100 kPa, 1 bar, 14.5 psi, 0.9869 atm). In a preferred embodiment, the catalyst-alkane feed contact time is in the range of 5-60 seconds, preferably 10-50 seconds, preferably 20-45 seconds, more preferably 30-40 seconds. In a preferred embodiment, the catalyst loading or amount of catalyst present in the oxidative dehydrogenation reaction is in the range of 0.01-0.5 g of catalyst per mL of alkane feed injected, preferably 0.05-0.45 g/mL, preferably 0.1-0.4 g/mL, preferably 0.15-0.3 g of catalyst per mL of alkane feed injected. The conditions may vary from these ranges and still provide acceptable conditions for performing the oxidative dehydrogenation of an alkane to a corresponding olefin utilizing the dehydrogenation catalyst of the present disclosure.

Oxidative dehydrogenation catalysts are evaluated for their percent conversion of the alkane as well as their selectivity to a product (i.e. the corresponding olefin or $CO_x$ (CO and/or $CO_2$). The definitions used in calculating the conversion and selectivity are represented for the method of the present disclosure using the oxidative dehydrogenation catalyst are represented in formula (V) and formula (VI) respectively.

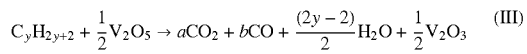

$$\text{Conversion of alkane} = \frac{\text{Moles of alkane converted}}{\text{Moles of alkane fed}} \times 100\% \quad (V)$$

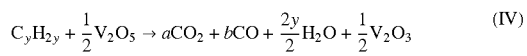

$$\text{Selectivity to product} = \frac{\text{Moles of product}}{\text{Moles of alkane reacted} - \text{Moles of product}} \times 100\% \quad (VI)$$

In one embodiment, the method of the present disclosure has an oxidative dehydrogenation alkane conversion rate as defined with formula (V) of up to 50%, preferably up to 45%, preferably up to 40%, preferably up to 35%, such as for example 5-50%, preferably 10-45%, preferably 12-40%, more preferably 15-35% and at least 5%, preferably at least 10%, preferably at least 20%, preferably at least 40%, preferably at least 45%. In another embodiment, the alkane is ethane, propane, or butane and the method has an alkane conversion of up to 50%, preferably up to 45%, preferably up to 40%, preferably up to 35%, such as for example 5-50%, preferably 10-45%, preferably 12-40%, more preferably 15-35%. In a preferred embodiment, the alkane is ethane and the corresponding olefin is ethylene and the method is performed with a catalyst-alkane feed contact time or reaction time of 5-60 seconds at a reaction dehydrogenation temperature of 500-600° C. and the method has an ethane conversion of 5-35%, preferably 20-30%, preferably 22-28%.

In one embodiment, the method of the present disclosure has an oxidative dehydrogenation olefin selectivity as defined with formula (VI) of at least 60%, preferably at least 65%, preferably at least 70%, preferably at least 75%, preferably at least 80%, preferably at least 85%, preferably at least 90%, preferably at least 95% such as for example 60-90%, preferably 61-85%, preferably 62-75%, more preferably 63-70%. In another embodiment, the alkane is ethane, propane, or butane and the method has an olefin selectivity of at least 60%, preferably at least 65%, preferably at least 70%, preferably at least 75%, preferably at least 80%, preferably at least 85%, preferably at least 90%, preferably at least 95% such as for example 60-90%, preferably 61-85%, preferably 62-75%, more preferably 63-70%. In a preferred embodiment, the alkane is ethane and the corresponding olefin is ethylene and the method is performed with a catalyst-alkane feed contact time or reaction time of 5-60 seconds at a reaction dehydrogenation temperature of 500-600° C. and the method has an ethylene selectivity of 60-90%, preferably 61-85%, preferably 62-75%, more preferably 63-70%. In a preferred embodiment, the method of the present disclosure has a $CO_2$ selectivity that is less than the olefin selectivity, and the $CO_2$ selectivity is less than 70%, preferably less than 60%, preferably less than 55%, preferably less than 50%. In a preferred embodiment, the method of the present disclosure has a CO selectivity that is less than the olefin selectivity and less than the $CO_2$ selectivity and the CO selectivity is less than 33%, preferably less than 30%, preferably less than 25%, preferably less than 20%.

In a preferred embodiment, the method of the present disclosure and alkane oxidative dehydrogenation (ODH) reactions incorporating the dehydrogenation catalyst described herein are performed in an oxygen-free environment or atmosphere. The presence of excess oxygen inside the reactor or catalyst chamber increases the combustion reaction and therefore $CO_x$ production. Preferably, the amount of oxygen available for the reaction is controlled by the catalyst available. By this method, by reducing the catalyst loading or increasing the alkane feed to catalyst ratio one can further minimize the available oxygen and decrease the combustion reaction, thus enhancing olefin selectivity.

In a preferred embodiment, the reactor is a fluidized bed reactor. As used herein, a fluidized bed reactor (FBR) is a type of reactor device that can be used to carry out a variety of multiphase chemical reactions. In this type of reactor, a fluid (gas or liquid) is passed through a granular solid material (usually a catalyst, preferably spherically shaped) at high enough velocities to suspend the solid and cause it to behave as though it were a fluid. This process, known as fluidization, imparts many important advantages to the fluidized bed reactor. It is equally envisaged that the method of the present disclosure may be adapted to be performed in a fixed-bed reactor, but this generally results in lower oxidative dehydrogenation catalyst activity.

The solid substrate (the catalytic material upon which the chemical species react) material in a fluidized be reactor is typically supported by a porous plate known as a distributor, distributor plate or sparger distributor. The fluid is then forced through the distributor up through the solid material. At lower fluid velocities, the solids remain in place as the fluid passes through the voids in the material. This is referred to as a packed bed reactor. As the fluid velocity is increased, the reactor will reach a stage where the force of the fluid on the solids is enough to balance the weight of the solid material. This stage is referred to as incipient fluidization and occurs at this minimum fluidization velocity. Once this minimum velocity is surpassed, the contents of the reactor bed begin to expand and swirl around similar to an agitated tank or boiling pot of water. The reactor is now a fluidized bed. Depending on the operating conditions and properties of the solid phase various flow regimes can be observed in this type of reactor.

The fluidized bed reactor technology has many inherent advantages including, but not limited to, uniform particle mixing, uniform temperature gradients and the ability to operate the reactor in continuous state. Due to the intrinsic fluid-like behavior of the solid material, fluidized beds do not experience poor mixing as in packed beds. The complete mixing allows for a uniform product that can often be hard to achieve in other reaction designs. The elimination of radial and axial concentration gradients also allows for better fluid-solid contact, which essential for reaction efficiency and quality. Many chemical reactions required the addition or removal of heat. Local hot or cold spots within the reaction bed, often a problem in packed beds, are avoided in fluidized conditions such as the fluidized bed reactor. In other reactor types, these local temperature differences, especially hot spots, can result in product degradation. Thus fluidized bed reactors are well suited to exothermic reactions. The bed-to-surface heat transfer coefficients for fluidized bed reactors are also high. The fluidized bed nature of these reactors allows for the ability to continuously withdraw product and introduce new reactants into the reaction vessel. Operating at a continuous process state allows for the more efficient production and removes startup conditions in batch processes.

Figure 13:
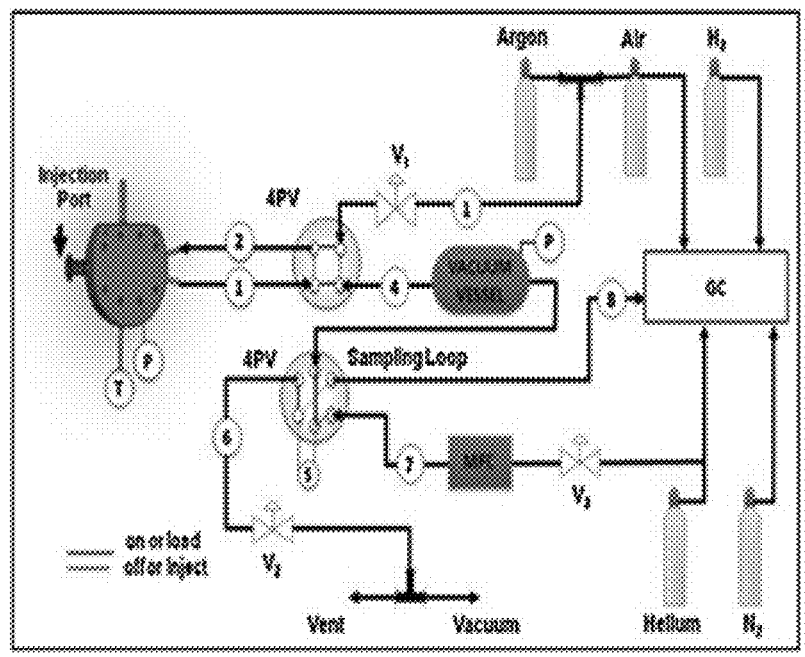
FIG. 13 is a schematic diagram of the CREC riser simulator experimental set-up.

In certain embodiments, the fluidizability, reactivity, and stability of the catalyst of the present disclosure may be demonstrated or evaluated in a Plexiglas unit with dimensions matching that of a CREC riser simulator (FIG. 13). This type of reactor has a capacity of 50-60 $cm^3$, preferably 51-55 $cm^3$ or about 53 $cm^3$ and is a batch unit designed for catalyst evaluation and kinetic studies under fluidized bed reactor conditions. The major components of the CREC riser simulator (FIG. 14) include, but are not limited to, a vacuum box, a series of sampling valves, a timer, two pressure transducers and three temperature controllers. The product gas may be analyzed by gas chromatography (GC) with a thermal conductivity detector (TCD) and flame ionization detector.

The oxidative dehydrogenation method of the present disclosure may be performed at various temperatures and contact times. In one embodiment, the contact times may be chosen to be consistent with catalyst reduction temperature reported by temperature programmed reduction (TPR) analysis. In a typical procedure, the oxidized catalyst sample of the present disclosure is into the reactor basket and the reactor basket is checked for potential leaks. Following the leak test the system is purged by flowing pure inert gas, preferably nitrogen or argon, most preferably argon. The temperature program is started to heat the reactor to the desired temperature. The inert gas flow is maintained to keep the reactor from any interference of gas phase oxygen. Once the reactor reaches a desired temperature, the inert gas flow is discontinued and the reactor isolation valve is closed once a desired pressure level is reached. A vacuum pump may be used to evacuate the vacuum box down to less than 100 kPa, preferably less than 50 kPa, preferably less than 25 kPa. In one embodiment, the catalyst may be fluidized by rotating agitation, preferably by an impeller at a speed of 100-5000 rpm, preferably 1000-4500 rpm, preferably 2000-4250 rpm, preferably 3000-4000 rpm. In another embodiment, no agitation (i.e. 0 rpm) is necessary to fluidize the catalyst. The alkane feed is injected into the reactor using a preloaded gas tight syringe and the reaction proceeds for a pre-specified amount of time. At the termination point, the isolation valve between the reactor and vacuum box may automatically open and transfer all reactant and products to the vacuum box for analysis.

In a preferred embodiment, the method for the dehydrogenation of an alkane to a corresponding olefin utilizing the dehydrogenation catalyst of the present disclosure in any of its embodiments further comprises i) oxidizing the reduced catalyst in an oxygen environment separated from the catalyst chamber to regenerate the dehydrogenation catalyst of the present disclosure and ii) repeating the flowing and the oxidizing at least once without a loss in percent conversion of the alkane, a loss in selectivity for the olefin, or both. In this manner, the dehydrogenation catalyst can be recovered and reused in at least 2 reaction iterations, preferably at least 3, preferably at least 4, preferably at least 5, preferably at least 6, preferably at least 10, preferably at least 15, preferably at least 20 reaction iterations. The dehydrogenation catalyst of the present disclosure can be reformed or regenerated from the reduced catalyst; in this case the regeneration is the oxidation of the reduced vanadium species on the support surface. In a preferred embodiment, the regeneration is oxidation under air flow of the reduced catalyst and is performed at a temperature of up to 700° C., preferably up to 600° C., preferably up to 500° C., preferably up to 400°

C. for a period of time of up to 30 minutes, preferably up to 20 minutes, preferably up to 15 minutes, preferably up to 10 minutes, preferably up to 5 minutes. In one embodiment, the reduced catalyst can flow out of the catalyst chamber to an additional chamber, be exposed to air flow to regenerate the dehydrogenation catalyst, and flow back to catalyst chamber for use in subsequent reaction iterations (FIG. 1). In a preferred embodiment, catalyst performance remains stable in cycles in terms of alkane conversion and olefin selectivity indicating the catalyst's ability to be regenerated which confirms catalyst stability at high temperatures.

In one embodiment, there is a less than a 10% change in percent alkane conversion between the first and second iteration, preferably less than 5%, preferably less than 4%, preferably less than 3%, preferably less than 2% change in percent alkane conversion between the first and second iteration. In another embodiment, there is a less than a 15% change in percent alkane conversion, preferably less than 10%, preferably less than 5%, preferably less than 2% change in percent alkane conversion between the first and twentieth iteration, preferably between the first and fifteenth iteration, preferably between the first and tenth iteration, preferably between the first and fifth iteration, preferably between the first and fourth iteration, preferably between the first and third iteration, preferably between the first and second iteration. In one embodiment, there is a less than a 10% change in percent olefin selectivity between the first and second iteration, preferably less than 5%, preferably less than 4%, preferably less than 3%, preferably less than 2% change in percent olefin selectivity between the first and second iteration. In another embodiment, there is a less than a 15% change in percent olefin selectivity, preferably less than 10%, preferably less than 5%, preferably less than 2% change in percent olefin selectivity between the first and twentieth iteration, preferably between the first and fifteenth iteration, preferably between the first and tenth iteration, preferably between the first and fifth iteration, preferably between the first and fourth iteration, preferably between the first and third iteration, preferably between the first and second iteration.

The examples below are intended to further illustrate methods protocols for preparing and characterizing the dehydrogenation catalyst of the present disclosure. Further, they are intended to illustrate assessing the properties and performance of these dehydrogenation catalysts. They are not intended to limit the scope of the claims.

EXAMPLE 1

Catalyst Synthesis

The impregnation technique was employed in the synthesis of catalyst samples. Alumina (pure activated alumina AA-100, surface area of 260 m²/g) was used as catalyst support. In order to prevent alumina phase transformation at high temperature during the oxidative dehydrogenation reaction, alumina was modified by the addition of 1% lanthanum (La). Before the impregnation, the support particles were calcined at 400° C. for 4 hr, then the support was impregnated at room temperature with a solution of V(AcAc)$_3$ and niobium (V) chloride in 100 mL toluene (0.153 M). The solution was stirred for 12 hr and then filtered and separated from the solvent. The resulting cake was dried at 150° C. for 24 hr. Catalyst precursors were reduced under hydrogen gas flow (10% H$_2$, 90% Argon) at 600° C. for a 6 hr period. Finally, catalyst samples were oxidized under airflow at 500° C. for 5 hr and as a confirming result samples turned to a yellow color indicating the presence of vanadium oxide on the catalyst surface.

EXAMPLE 2

X-Ray Fluorescence (XRF) and BET Surface Area Catalyst Characterization

X-ray fluorescence (XRF) analysis was used to determine the elemental composition of each sample. A Bruker Tornado M4 micro-ed XRF analyzer was used, which was equipped with a single high performance XFlash detector and a 25 μm diameter spot size. N$_2$ adsorption/desorption of 1% La—VO/Al$_2$O$_3$ and 1% La-3% Nb—VO$_x$/Al$_2$O$_3$ catalyst samples were determined in a Quantachrome ASIQwin, by using nitrogen adsorption at 77 K. For each experiment, an amount of 0.40-0.50 g of catalyst was used; samples were degassed at 350° C. for 2 hr before analysis. The adsorption isotherms were plotted with a 0.04-1 relative pressure range.

Figure 2:
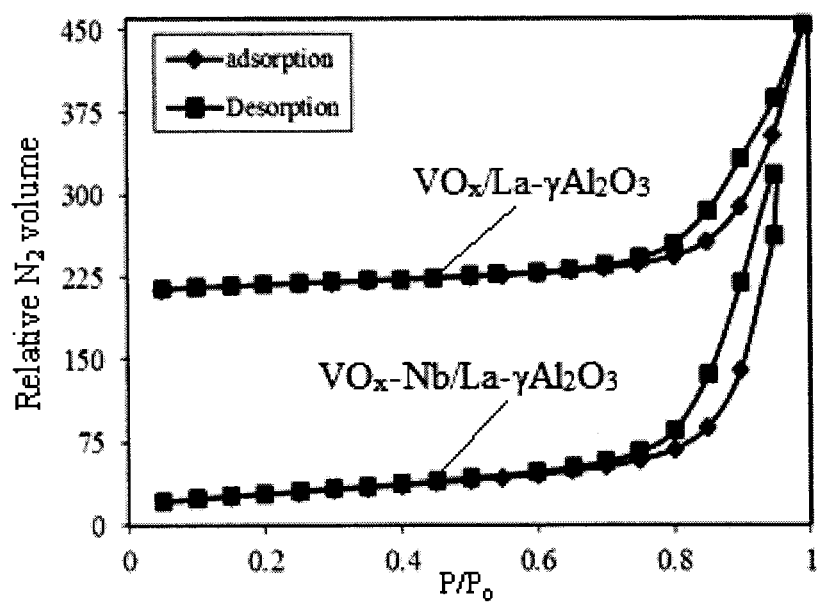
FIG. 2 is a $N_2$ adsorption/desorption isotherm for (i) VOx/La-$\gamma Al_2O_3$ catalyst and a $N_2$ adsorption/desorption isotherm for (ii) $VO_x$—Nb/La-$\gamma Al_2O_3$ catalyst.

The BET surface area of the prepared catalyst samples were determined using N$_2$ adsorption isotherm data. FIG. 2 shows adsorption/desorption isotherms of two catalyst samples, where the volume of adsorbed/desorbed N$_2$ is plotted versus relative pressure. The curves follow Type (V) isotherm behavior, which suggests a narrow size mesoporosity of the catalyst materials [A. M. Elfadly, A. M. Badawi, F. Z. Yehia, Y. A. Mohamed, M. A. Betiha, and A. M. Rabie, "Selective nano alumina supported vanadium oxide catalysts for oxidative dehydrogenation of ethylbenzene to styrene using CO2 as soft oxidant," Egypt. J. Pet., vol. 22, no. 3, pp. 373-380, December 2013.—incorporated herein by reference in its entirety]. The VO$_x$—Nb/La—Al$_2$O$_3$ and VO$_x$/La—Al$_2$O$_3$ samples display a Type-V isotherm. This indicates a narrow size mesoporosity and a nitrogen monolayer adsorption on the catalyst surface as shown in FIG. 2. The observed nitrogen monolayer coverage is a good indicator of the support preserving the original surface area and as a result, a high VO$_x$ dispersion. For both the samples, the monolayer coverage extended even beyond 0.75 relative pressures, which indicates a good dispersion of active sites. The monolayer volume of the adsorbed nitrogen was calculated according to formula (VII) using BET surface area.

$$V_m = \frac{S_{BET}}{A_m \times N} \times 22400 \quad \text{(VII)}$$

In this formula, $S_{BET}$ is the BET surface area in m², N is Avogadro's constant in molecule/mol, $A_m$ is the volume occupied by one N$_2$ gas molecule (0.162 m²) and $V_m$ is the monolayer volume in mL per gram of catalyst. Table 1 presents the BET surface area and monolayer volume of the synthesized catalysts. It shows that the elemental compositions are within a ±2% margin of error of the targeted compositions.

TABLE 1

X-ray fluorescence (XRF) and BET surface area results

| Sample | V (%) | La (%) | Nb (%) | O$_2$ (%) | Al (%) | BET Surface Area (m²/g - cat.) | Monolayer (mL/g-cat.) |
|---|---|---|---|---|---|---|---|
| VO$_x$/La—γAl$_2$O$_3$ | 14.1 | 0.93 | — | 43.4 | 41.64 | 16.5 | 3.78 |
| VO$_x$—Nb/La—γAl$_2$O$_3$ | 13.8 | 0.87 | 3.21 | 45.6 | 36.52 | 24.17 | 5.53 |

Targeted compositions: La: 1 wt %; Nb: 3 wt %; and V: 15 wt %.

EXAMPLE 3

X-Ray Diffraction (XRD) Catalyst Characterization

X-ray diffraction (XRD) analysis was used to identify the crystallographic structure of the catalyst samples. XRD patterns of all catalysts reported herein were recorded on a Rigaku miniflex diffractometer with monochromatic Cu and Kα radiation (λ=0.15406 nm, 30 kV, 15 mA) using the normal scan rate of 2°/min. X-rays were collimated using a 1.25° divergent scattering slit, and a 0.13 mm receiving slit. Samples were scanned within 2θ range of 20-80° with a step size of 0.005°.

Figure 3:
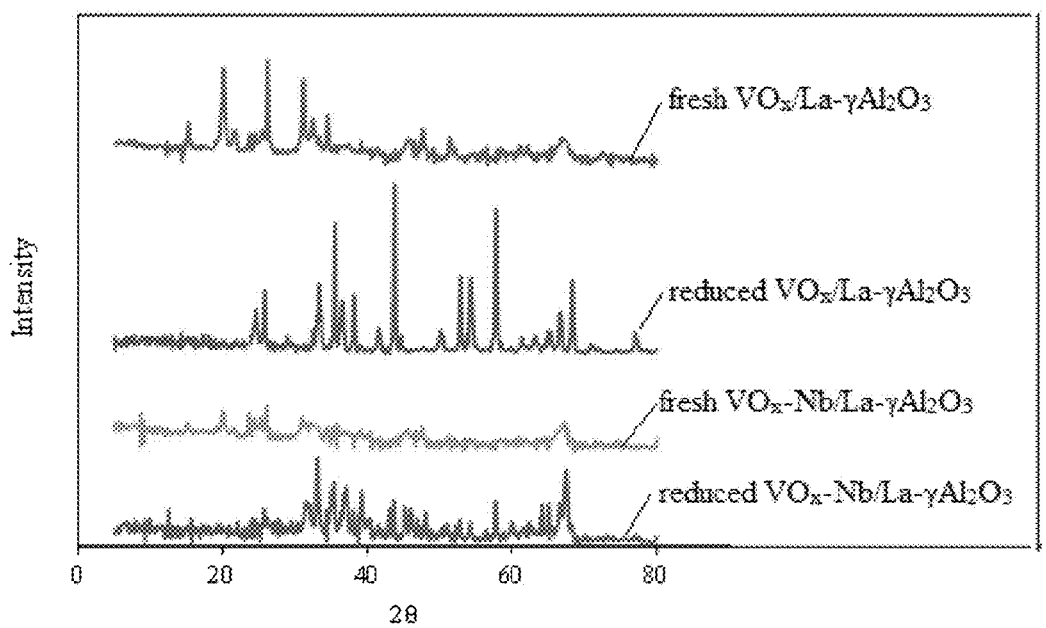
FIG. 3 is an X-ray diffraction (XRD) spectrum of (i) fresh $VO_x$/La-$\gamma Al_2O_3$ catalyst, an XRD spectrum of (ii) reduced $VO_x$/La-$\gamma Al_2O_3$ catalyst, an XRD spectrum of (iii) fresh $VO_x$—Nb/La-$\gamma Al_2O_3$ and an XRD spectrum of (iv) reduced $VO_x$—Nb/La-$\gamma Al_2O_3$ catalyst.

The XRD patterns of fresh and reduced catalyst samples, $VO_x/La-\gamma Al_2O_3$ and $VO_x$—$Nb/La-\gamma Al_2O_3$, are shown in FIG. 3. In both catalyst samples, the peaks in the 2θ range of 0° to 300 are due to the $VO_x$ species [E. V. Kondratenko, O. Ovsitser, J. Radnik, M. Schneider, R. Kraehnert, and U. Dingerdissen, "Influence of reaction conditions on catalyst composition and selective/non-selective reaction pathways of the ODP reaction over V2O3, VO2 and V2O5 with O2 and N2O," *Appl. Catal. A Gen.*, vol. 319, pp. 98-110, 2007.—incorporated herein by reference in its entirety]. The small amounts of Nb and La oxides added to the catalysts are in the form of a small crystal phase which is not detectable by XRD. In the unpromoted $VO_x/La-\gamma Al_2O_3$ sample, the V—V bond or polyvanadate and bulk vanadate are present, as these peaks are consistent with the bulk vanadate XRD pattern. On the other hand, with $VO_x$—$Nb/La-\gamma Al_2O_3$ sample the Vanadium species are present as mono-vanadate forming a monolayer on the catalyst surface. The addition Nb prevents V—V bond formation in the $VO_x$—Nb/La-$\gamma Al_2O_3$ sample. FIG. 3 shows the XRD patterns of reduced catalysts samples. New $VO_x$ peaks were detected such as $VO_2$, which confirms $V_2O_5$ reduction occurs in several steps.

EXAMPLE 4

Scanning Electron Microscopy (SEM) and Catalyst Morphology Characterization

The shape and morphology of catalyst sample particles was examined by scanning electron microscopy (F-SEM, Tescan Lyra-3). A high performance focused ion beam (FIB) was used together with energy-dispersive X-ray spectroscopy (EDX) to get a qualitative compositional analysis. Samples were prepared by Au coating of 5 nm thickness. Image magnification was displayed using a voltage of 20 Kv.

Figure 4:
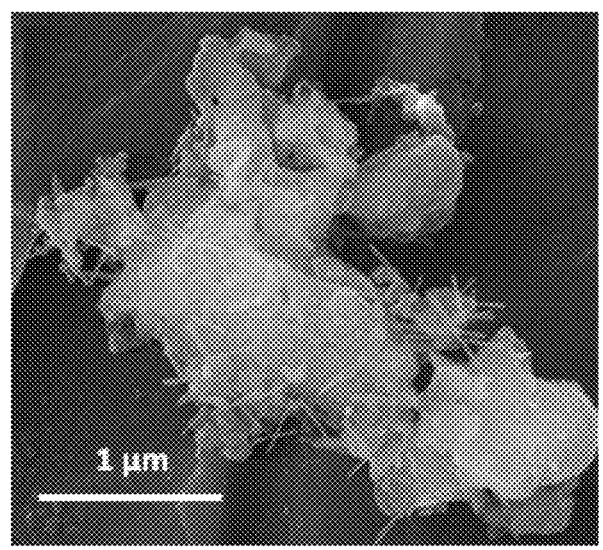
FIG. 4 is a scanning electron microscopy (SEM) image of fresh 1% La-15% VOx/Al$_2$O$_3$ catalyst sample.
Figure 5:
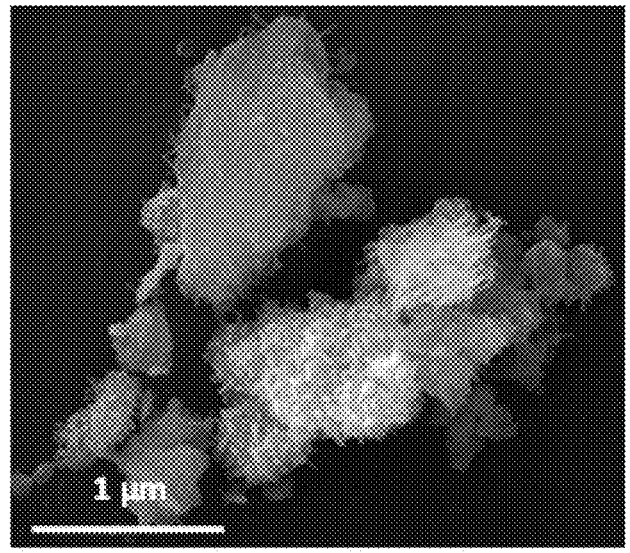
FIG. 5 is a SEM image of fresh 1% La-3% Nb-15% VOx/Al$_2$O$_3$ catalyst sample.

FIG. 4 and FIG. 5 show scanning electron microscopy (SEM) images with magnification of 50 kx of fresh samples of $VO_x/La-\gamma Al_2O_3$ and $VO_x$—$Nb/La-\gamma Al_2O_3$ catalysts which calcinated at 500° C. respectively. The SEM images reveal that sample particles are present in non-uniform size and shape. $LaO_2$ and $Nb_2O_5$ appear as crystal phases, which enhance the isolation of vanadium species on the surface of alumina as confirmed by the XRF elemental analysis (Table 1). Mixed metal oxides as well as bulk vanadate are not present, a similar conclusion may be drawn by Raman analysis as described below as well as with previous results reported in the literature [I. Levin and D. Brandon, "Metastable Alumina Polymorphs: Crystal Structures and," vol. 2012, no. 1998, pp. 1995-2012, 2012.—incorporated herein by reference in its entirety]. The pH of the impregnation solution and the support surface affect the nature of vanadium oxide on the support. $Al_2O_3$ has a surface pH of 8.9 which will result in polyvanadate formation (the V—O—V bond) but thermal treatment converts polyvanadate to mono-vanadate [Y. H. Kim and H. Lee, "Redox Property of Vanadium Oxide and Its Behavior in Catalytic Oxidation," vol. 20, no. 12, 1999.—incorporated herein by reference in its entirety].

Figure 6:
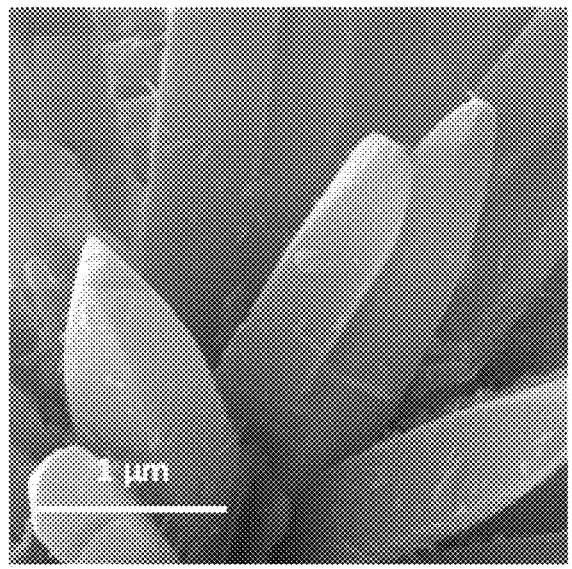
FIG. 6 is a SEM image of reduced 1% La-15% VO$_x$/Al$_2$O$_3$ catalyst sample using H$_2$ flow at 750° C.
Figure 7:
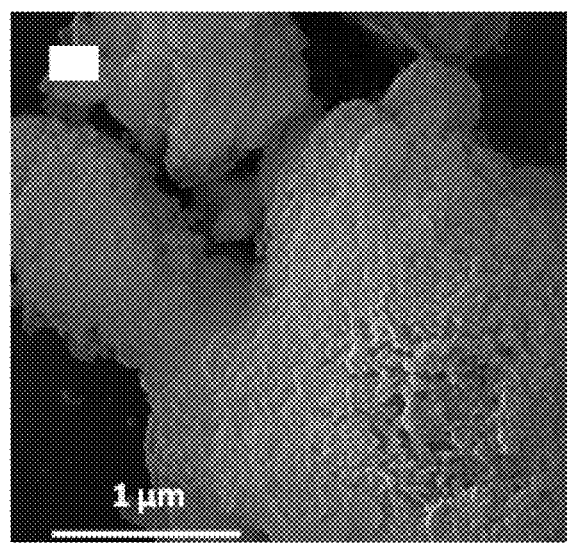
FIG. 7 is a SEM image of reduced 1% La-3% Nb-15% VOx/Al$_2$O$_3$ catalyst sample using H$_2$ flow at 750° C.

FIG. 6 and FIG. 7 show SEM images for the reduced samples of 1% La-15% $VO_x/Al_2O_3$ and 1% La-3% Nb-15% $VO_x/Al_2O_3$ catalysts respectively, which were reduced at 750° C. under $H_2$ flow. After reduction, vanadium oxides, such as $VO_2$, are likely to be present. This is also shown in the temperature programmed reduction (TPR) analysis described below, wherein the results show multiple peaks appearing due to the existence of many forms of vanadium oxides. Additionally, $VO_2$ can be in the form of long rods [P. Liu, K. Zhu, Y. Gao, Q. Wu, J. Liu, J. Qiu, Q. Gu, and H. Zheng, "Ultra-long VO2 (A) nanorods using the high-temperature mixing method under hydrothermal conditions: synthesis, evolution and thermochromic properties," *CrystEngComm*, vol. 15, no. 14, p. 2753, 2013; and B. Mitra, I. E. Wachs, and G. Deo, "Promotion of the propane ODH reaction over supported V2O5/Al2O3 catalyst with secondary surface metal oxide additives," *J. Catal.*, vol. 240, no. 2, pp. 151-159, June 2006; and X. Chen, Y. Liu, G. Niu, Z. Yang, M. Bian, and A. He, "High temperature thermal stabilization of alumina modified by lanthanum species," *Appl. Catal. A Gen.*, vol. 205, no. 1-2, pp. 159-172, January 2001.—each incorporated herein by reference in its entirety].

EXAMPLE 5

Raman Spectroscopy Catalyst Characterization

Raman spectroscopy was collected with an Yvon Jobin analyzer equipped with a cooled iHR320 Horiba spectrometer with a charge-coupled device (CCD) detector that removes the elastic laser scattering. The laser source was green type at 532 nm and a laser intensity of 50%, with a 96 slit width and a 50-2500 spectrum window.

Figure 8:
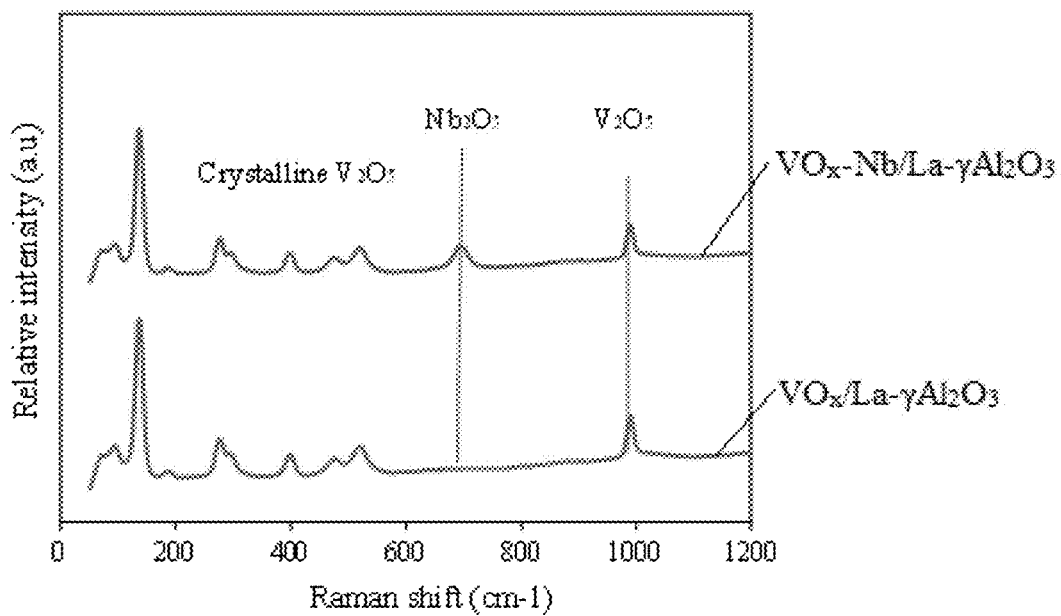
FIG. 8 is a Raman spectrum of (i) VO$_x$/La-γAl$_2$O$_3$ catalyst and a Raman spectrum of (ii) VO$_x$—Nb/La-γAl$_2$O$_3$ catalyst.

The vanadium oxide species on support surface were examined using Raman spectroscopy. The vibrational Raman spectra of catalyst samples are shown in FIG. 8. Raman analysis confirmed that there are many forms of $VO_x$ present on the support surface. Sharp peaks at 132 cm$^{-1}$ arise from the vibration of $V_6O_{13}$ [X. Wang, H. Li, Y. Fei, X. Wang, Y. Xiong, Y. Nie, and K. Feng, "XRD and Raman study of vanadium oxide thin films deposited on fused silica substrates by RF magnetron sputtering," *Appl. Surf Sci.*, vol. 177, no. 1-2, pp. 8-14, June 2001.—incorporated herein by reference in its entirety]. In addition, literature reports that peaks in the range of 200 cm$^{-1}$ to 600 cm$^{-1}$ are from vibrations of crystalline $V_2O_5$. Furthermore, the V—O—V bond is a result of these crystalline $V_2O_5$ species and their formation represent catalyst active sites. In addition, peaks at 995 cm$^{-1}$ are due to the V=O bond which is also related to $V_2O_5$ in isolated form [I. E. Wachs, "Catalysis science of supported vanadium oxide catalysts," Dalton Trans., vol. 42, no. 33, pp. 11762-9, September 2013.—incorporated herein by reference in its entirety]. It can be seen clearly that both samples in FIG. 8 have relatively high vanadia loading and thus exhibit sharp peaks in the range of crystalline $V_2O_5$. This is in agreement with previous studies that have indicated that increasing metal loading to certain levels can lead to the formation of polyvandate species.

Consequently, vanadium loading to some extent forms monolayer on the support surface. This monolayer consists mainly of V—O and V=O bonds which are mainly responsible for the formation of isolated vanadia species on the support surface [A. A. N. N. Mcconnell and C. N. R. Rao, "I % arxan spectra of Robin oxides," vol. 32, 1976; and R.

Bulánek, P. Čičmanec, and M. Setnicka, "Possibility of VOx/SiO2 Complexes Speciation: Comparative Multi-wavelength Raman and DR UV-vis Study," *Phys. Procedia*, vol. 44, pp. 195-205, January 2013; and M. Martinezhuerta, X. Gao, H. Tian, I. Wachs, J. Fierro, and M. Banares, "Oxidative dehydrogenation of ethane to ethylene over alumina-supported vanadium oxide catalysts: Relationship between molecular structures and chemical reactivity," *Catal. Today*, vol. 118, no. 3-4, pp. 279-287, December 2006.—each incorporated herein by reference in its entirety]. A surface vanadium oxide layer on oxide supports is more likely to be formed than crystalline $V_2O_5$ due to the surface mobility of vanadium oxide and the lower surface free energy of crystalline $V_2O_5$ (8-9×10$^{-6}$ J cm$^{-2}$) relative to supports ($Al_2O_3$~68-70×10$^{-6}$ J cm$^2$; $ZrO_2$~59-80×10$^{-6}$ J cm$^{-2}$; $TiO_2$~28-38×10$^{-6}$ J cm$^{-2}$) [H. Knozinger and E. Taglauer, "No Title," catalysis, vol. 10, no. 1, 1993; and P. O. F. We, J. A. T. Solid, and S. Interface, "J. HABER, T. MACHEJ and T. CZEPPE," vol. 151, pp. 301-310, 1985.—each incorporated herein by reference in its entirety]. $Nb_2O_5$ was detected in the range between 700 cm$^{-1}$ and 710 cm$^{-1}$, however treatment of the sample at temperatures higher than 500° C. may produce the crystal phase of $Nb_2O_5$ which may shift the Raman spectrum [J.-M. Jehng and I. E. Wachs, "Structural chemistry and raman spectra of niobium oxides," *Chem. Mater.*, vol. 3, no. 1, pp. 100-107, 1991.—incorporated herein by reference in its entirety].

EXAMPLE 6

Temperature Programmed Reduction-Oxidation (TPR/TPO) Characterization of Catalyst Reducibility and Oxygen Carrying Capacity Catalyst samples were characterized using temperature programmed reduction/oxidation (TPR/TPO) characterization techniques. Experiments were conducted using the AutoChem II ASAP 2920 analyzer. The purposes of TPR/TPO cycles are to determine catalyst oxygen carrying capacity, activity temperature ranges, and maximum activity temperature and catalyst stability during reduction-oxidation cycles. It has been reported that during reduction/oxidation cycles at high temperature vanadia dispersion changes which affects the $VO_x$ phases on the support surface and thus catalyst activity [F. Klose, T. Wolff, H. Lorenz, a Seidel-morgenstern, Y. Suchorski, M. Piorkowska, and H. Weiss, "Active species on γ-alumina-supported vanadia catalysts: Nature and reducibility," *J. Catal.*, vol. 247, no. 2, pp. 176-193, April 2007; and M. Argyle, "Effect of Catalyst Structure on Oxidative Dehydrogenation of Ethane and Propane on Alumina-Supported Vanadia," *J. Catal.*, vol. 208, no. 1, pp. 139-149, May 2002.—each incorporated herein by reference in its entirety].

The TPR/TPO test procedure was conducted as follows; Argon (99.9%) was introduced at a rate of 50 mL/min while temperature was gradually increased to 300° C. for a period of 3 hours. The temperature was reduced to ambient and an $H_2$ Argon gas mixture (10% $H_2$) was circulated to reduce the sample at a rate of 50 mL/min while the temperature was gradually elevated to 750° C. at a heating rate of 10° C./min. A thermal conductivity detector (TCD) was used to measure $H_2$ concentration change and the signal was later calibrate to a volume of $H_2$ consumed by the catalyst (cc/g).

Figure 9:
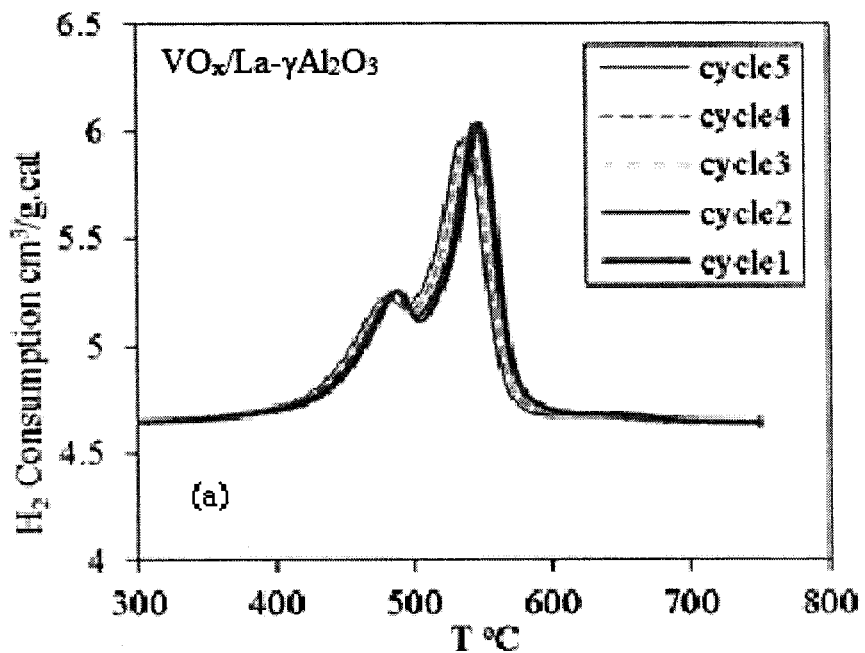
FIG. 9 is a temperature programmed reduction (TPR) and temperature programmed oxidation (TPO) cycle profile for VO$_x$/La-γAl$_2$O$_3$ catalyst sample.
Figure 10:
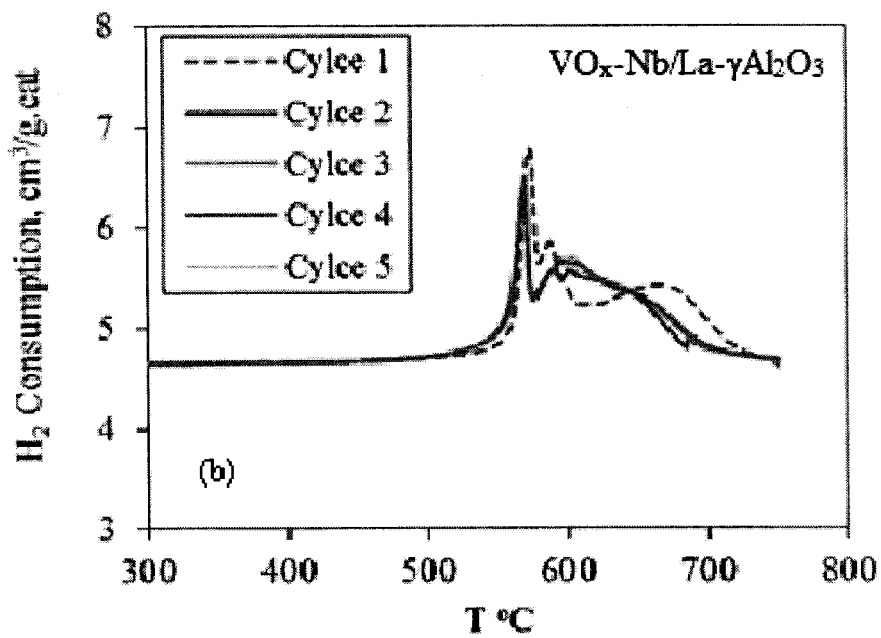
FIG. 10 is a TPR and TPO cycle profile for VO$_x$—Nb/La-γAl$_2$O$_3$ catalyst sample.

FIG. 9 and FIG. 10 show TPR profiles of $VO_x$/La-γ$Al_2O_3$ and $VO_x$—Nb/La-γ$Al_2O_3$ catalyst samples respectively. The integration of the area under the TPR profile curve gives $H_2$ consumptions by the respective sample. It appears that the $H_2$ consumption by the Nb containing $VO_x$—Nb/La-γ$Al_2O_3$ samples (79 cm$^3$/g) is significantly higher than that of the $VO_x$/La-γ$Al_2O_3$. The higher hydrogen consumption of the Nb promoted samples can be attributed to Nb oxides that contribute to the additional lattice oxygen carrying capacity.

Both of the samples show multiple peaks indicating different vanadium oxides such as $V_2O_5$, $V_2O_3$, and $VO_2$. The vanadia phase on the solid support is present as surface vanadium oxide species below monolayer coverage and forms crystalline $V_2O_5$ particles above monolayer coverage. The oxide phase is responsible for the overall catalytic activity and selectivity, however the crystalline $V_2O_5$ phase only has a minor contribution on the catalyst only minimally effecting catalytic activity and selectivity. In regards to the mechanisms of vanadia species phase transformation, it was reported that these species are formed during the reduction of vanadium oxide, when oxygen vacancies are formed at the surface. Once the concentration of these vacancies surpasses a certain critical value, they aggregate into a vacancy disc, called the shear plane. Part of vanadium oxide may shear in such a manner that along the shear plane the linkage between trigonal bipyramids is changed from corner-sharing to edge-sharing. Thus, another stable structure is formed that is stoichiometrically different from the original structure. In addition, it is clear from the TPR results that the introduction of Nb shifted catalyst activity toward a higher temperature range (from 400-600° C. to 550-750° C.) while also increasing catalyst activity by enhancing the isolation of vanadium species.

In order to rule out the possibility of alumina thermal phase transformation, samples were exposed to temperatures up to 750° C. in the TPR/TPO cycles. The repeated TPR/TPO measurements also allow for the determination of the oxygen carrying capacity and the redox properties of the catalyst under study. It should be noted that the oxidative dehydrogenation catalyst oxygen carrying capacity is of great importance for oxidative dehydrogenation implementation in a fluidized bed process. The oxygen carrying capacity determines the circulation rate of the catalyst between twin fluidized bed reactors including an oxidative dehydrogenation reactor and the catalyst regenerator. Considering catalyst stability during reduction-oxidation (redox) cycles, both samples showed good stability, as seen in FIG. 9 and FIG. 10. As can be seen from FIG. 10 the performance of the sample containing Nb decreased slightly during the cycles which could be attributed to the effect of Nb causing formation of Nb vanadate which is a more difficult species to re-oxidize.

On the other hand, the sample without Nb has shown a consistent performance and the redox cycles are superimposed with the same patterns. FIG. 10 shows that the percentage of vanadium decreases over TPR reduction-oxidation cycles, the reacted hydrogen is calculated by calculating the TPR peak. The very close TPR profiles show a consistent metal reduction and confirm the good thermal stability of the $VO_x$—Nb/La—$Al_2O_3$ catalyst. As a result, it was hypothesized that the presence of La provides the thermal stability of the alumina support. The reduced vanadium is calculated as follows using formula (VIII).

$$\text{fraction reduced \%} = \frac{M_{W_v} \times V_{H_2}}{v \times V_g \times W_0} \times 100\% \quad \text{(VIII)}$$

In this formula, $W_v$ is the amount of reduced vanadium in g, $M_{wv}$ is the molecular weight of vanadium in g/mol, $V_{H2}$ is the volume of reacted hydrogen in cm$^3$ (at STP), $V_g$ is the molar volume of gas in mol/cm³ (at STP), $W_0$ is the initial weight of vanadium and v is the stoichiometric number of hydrogen based on the reaction stoichiometry of formula (IX).

$$V_2O_5 + 2H_2 \rightarrow V_2O_3 + 2H_2O \quad (IX)$$

Assuming that $V_2O_5$ is the initial reducible catalyst species present on the support, then the reduction reaction equation of formula (IX) applies.

The percentage of total reduction decreases over cycles as the $VO_x$ sites reduced decreases. However, the percentage of reduction was slightly increased in the Nb containing samples due to the increased number of isolated active $VO_x$ sites. Furthermore, the fraction reduced is a function of the volume of $H_2$ consumed each cycle (catalyst activity), which is affected by the number of available active sites. In addition, during reduction at high temperature, phase transformation can occur to the catalyst support as well as the $VO_x$ species on the surface. The phase change of VOx species is more crucial to the oxidative dehydrogenation reaction in which crystalline $VO_x$ is formed during the reduction/reaction cycles. These crystalline $VO_x$ formations reduce the number of surface active sites which ultimately reduces catalyst activity.

EXAMPLE 7

$NH_3$—Temperature Programmed Desorption ($NH_3$-TPD) Characterization of Catalyst Acidity The purposes of $NH_3$-TPD experiments are to determine the total catalyst acidity. TPD can also give an idea about metal-support interactions by modeling both $NH_3$ desorption kinetics. Furthermore, $NH_3$-TPD was utilized to determine the strength of acid sites available on the catalyst surface. $NH_3$-TPD experiments were conducted using the AutoChem II Analyzer from Micrometrics. The catalyst sample (between 0.15 and 0.20 g) was placed in a U-shaped quartz container and degassed for 2 hr at 300° C. in a flow of helium at 30 mL/min. The samples were then cooled to 120° C. and brought to saturation with ammonia using a $NH_3$/He gas mixture (4.55% $NH_3$) for one hour at a rate of 50 mL/min. Ammonia flow was stopped, and replaced by a He gas purge, fed at a rate of 50 mL/min. This was done for 1 hr at 120° C. to remove the physically adsorbed ammonia. Following this step, the temperature was raised to 500° C. at different heating rates (10, 20, and 30° C./min). As the temperature was gradually increased, ammonia desorbed as it gained enough energy to overcome the desorption barrier.

The TPD test was performed in the temperature range from 120-500° C. for both catalyst $VO_x$/La-$\gamma Al_2O_3$ and $VO_x$—Nb/La-$\gamma Al_2O_3$. Ammonia was considered due to its strong basicity and small molecular size. Ammonia also allows for the determination of total acidity and the strength of acid sites for a wide range of temperatures [I. Union, O. F. Pure, and A. Chemistry, "INTERNATIONAL UNION OF PURE MANUAL OF METHODS AND PROCEDURES FOR Manual of methods and procedures for catalyst characterization (Technical Report)," vol. 67, pp. 1257-1306, 1995.—included herein by reference in its entirety]. Overall, both samples exhibit similar behavior at different heating rates. Nb appears to have insignificant effects on the quality of catalyst acids sites; however, Nb addition shifted the curved of the TCD signal slightly downward as the total acidity decreased. Importantly, neither the type nor the strength changed significantly. Catalyst acidity strength appears clearly at the 20° C./min heating rate more so than either the 10° C./min or 15° C./min rates. It can be noticed that the first peaks for both catalysts occur at 195° C. (FIG. 11 and FIG. 12) indicating the desorption of $NH_3$ from weak acid sites and the second peak occurs at 375° C. for catalyst samples not containing Nb and at 415° C. for catalyst samples containing Nb. Although $NH_3$ was desorbed from strong acid sites, it seems clear that weak acid sites predominate and that may decrease the cracking of feed on the catalyst surface. Table 2 displays the total acidity of catalyst samples in mL of $NH_3$ per g of catalyst for different desorption heating rates.

TABLE 2

Total acidity of catalyst samples

| Sample | Heating rate (° C./min) | $NH_3$ ml/g-cat. |
|---|---|---|
| $VO_x$/La—$\gamma Al_2O_3$ | 10 | 9.15 |
|  | 15 | 9.8 |
| $VO_x$—Nb/La—$\gamma Al_2O_3$ | 10 | 7.2 |
|  | 15 | 8.65 |

Figure 11:
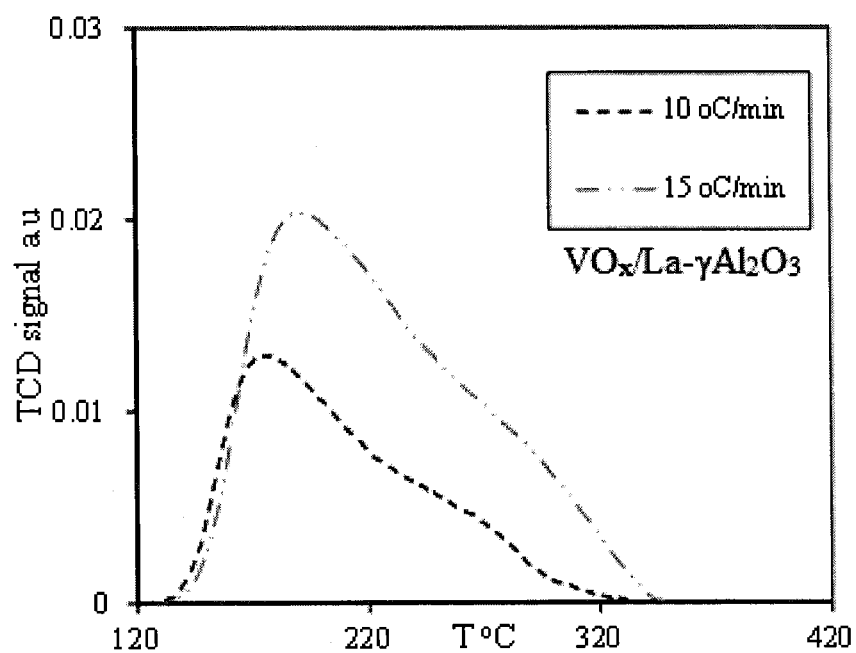
FIG. 11 is a temperature programmed desorption (TPD) of NH$_3$ profile for VOx/La-γAl$_2$O$_3$ catalyst sample.
Figure 12:
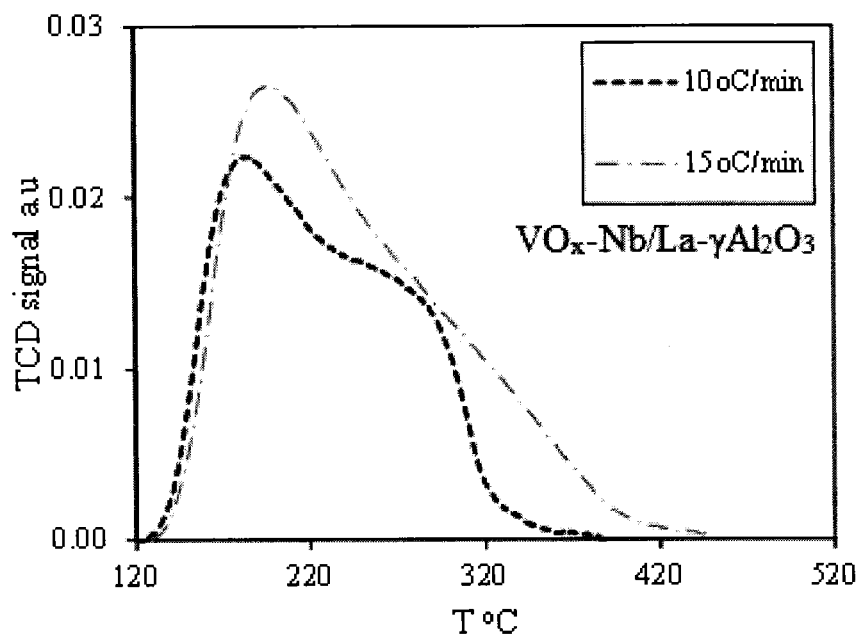
FIG. 12 is a TPD of NH$_3$ profile for VO—Nb/La-γAl$_2$O$_3$ catalyst sample.

The volume of ammonia adsorbed/desorbed was calculated from FIG. 11 and FIG. 12 by calculating the area under the curve by using appropriate calibration of TCD signal to a corresponding volume of ammonia concentration. The catalyst sample containing Nb shows lower ammonia adsorption/desorption behavior than the catalyst sample not containing Nb and therefore lowed total acidity. This data suggest that Nb decreased the catalyst acidity by covering some acid sites. Additionally, these catalyst samples have lower acidity than pure alumina, which has total acidity of about 14.39 mL $NH_3$ per g of ammonia [J. Mortensen, "Nitrogen Adsorption and Dissociation on Fe(111)," *J. Catal.*, vol. 182, no. 2, pp. 479-488, March 1999.—incorporated herein by reference in its entirety].

EXAMPLE 8

Catalyst Evaluation

Figure 14:
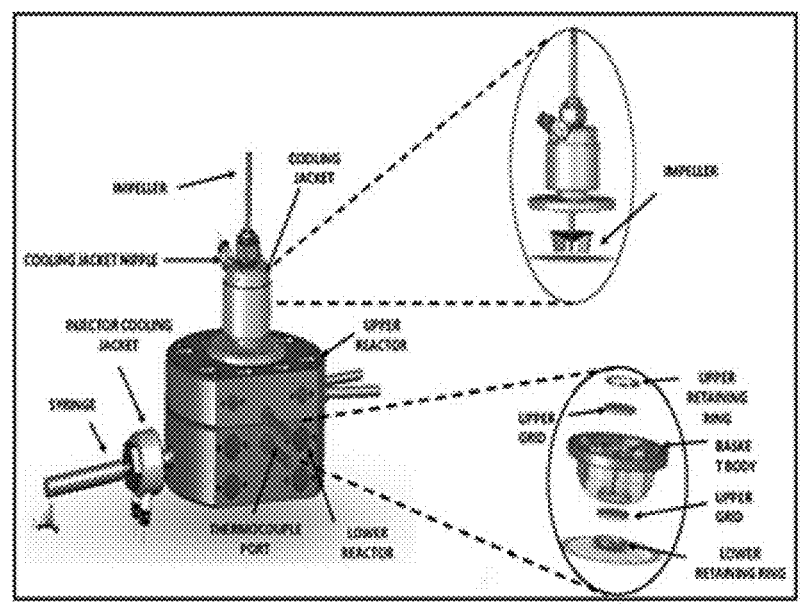
FIG. 14 is an overview of the CREC riser simulator reactor body.

The reactivity and the stability of the $VO_x$—Nb/La—$Al_2O_3$ catalyst samples were investigated using a CREC riser simulator (FIG. 13). The reactor has a capacity of 53 cm³. It is a batch unit designed for catalyst evaluation and kinetic studies under fluidized bed reactor conditions. The major components of the CREC riser simulator are shown in FIG. 14. These components include a vacuum box, a series of sampling valves, a timer, two pressure transducers and three temperature controllers. The product gas was analyzed by gas chromatography (GC) with a thermal conductivity detector (TCD) and a flame ionization detector (FID).

The oxidative dehydrogenation of ethane to ethylene experiments were conducted at various temperatures and contact times. The selected temperatures for the experiments were chosen to be consistent with reduction temperatures of the catalysts, as reported in the TPR analysis. In a typical run, 0.3 g of oxidized catalyst sample was loaded into the reactor basket and the reactor was checked for potential leaks. Following the leak test, the system was purged by flowing pure Argon. The temperature program was started to heat the reactor to the desired temperature. The argon flow was maintained to keep the reactor from any interference of gas phase oxygen.

Once the reactor reached the desired temperature, the argon flow was discontinued. The reactor isolation valve was closed when it had reached the desired pressure level. At this stage the vacuum pum was turned on to evacuate the vacuum box down to 20.7 kPa (3.75 psi). The catalyst was fluidized by rotating the impeller at a speed of 4000 rpm. At this point, the ethane feed was injected (3 mL) into the reactor by using a preloaded gas tight syringe. The reaction continued for a pre-specified amount of time. At the termination point, the isolation valve between the reactor and the vacuum box opened automatically and transferred all the reactant and products into the vacuum box. The gas samples in the vacuum bottle were analyzed using an Agilent 7890A GC equipped with bot a TCD and a FID detector. For each catalytic run, the product samples were analyzed three times to ensure the accuracy of the analysis. Finally, the product analysis data was used to calculate conversion and selectivity of various products. The following definitions were used in calculating the conversion and selectivity, formula (V) and formula (VI).

$$\text{Conversion of ethane} = \frac{\text{Moles of ethane converted}}{\text{Moles of ethane fed}} \times 100\% \quad (V)$$

$$\text{Selectivity of product } i = \frac{\text{Moles of product } i}{\text{Moles of ethane reacted} - \text{Moles of product } i} \times 100\% \quad (VI)$$

Figure 15:
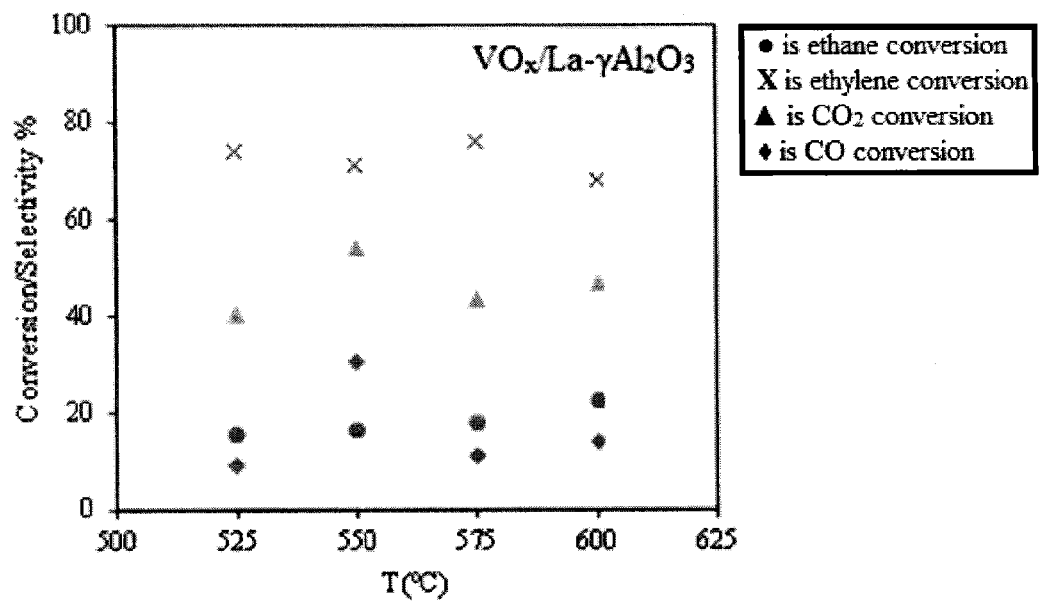
FIG. 15 shows the temperature effect on the oxidative dehydrogenation reaction for VO$_x$/La-γAl$_2$O$_3$ catalyst sample at a time of 10 s.
Figure 16:
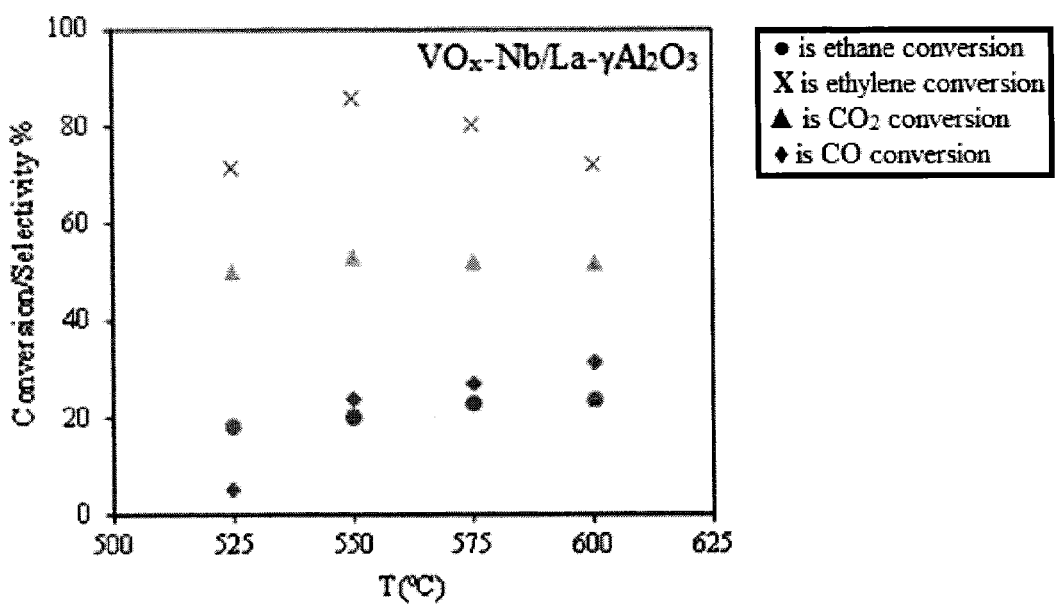
FIG. 16 shows the temperature effect on the oxidative dehydrogenation reaction for VO$_x$—Nb/La-γAl$_2$O$_3$ catalyst sample at a time of 10 s.

Catalyst performance was examined using the CREC-riser simulator under fluidized conditions and an oxygen free environment. The temperature effect was measured at a constant reaction time of 10 seconds and a temperature range from 525-600° C. as can be seen in FIG. 15 and FIG. 16. The catalyst modified by Nb gives ethane conversion up to 23.5%, which is higher than the catalyst sample without Nb addition. This indicates that Nb has increased catalyst activity in agreement with the TPR result (FIG. 10) where additional peaks were detected as more $H_2$ was consumed (i.e. the TCD signal in FIG. 12). It has been reported that metal oxides on the support contribute to the dehydrogenation reaction and therefore catalyst activity. Therefore, since Nb oxides were detected by Raman spectroscopy, Nb itself has a positive effect on catalyst activity.

In addition, catalyst selectivity has been increased significantly by the addition of Nb. FIG. 15b shows ethylene selectivity reach up to 76% at 775° C. for $VO_x/La-\gamma Al_2O_3$, which increased for the sample containing Nb up to 85.7% at the lower temperature of 550° C. as can be seen in FIG. 16. Since the reducibility of $VO_x$ species on the support surface can affect the selectivity, and Nb enhances the isolation of $VO_x$ species on the support surface it follows that Nb should ultimately enhance ethylene selectivity [P. Cong, a Dehestani, R. Doolen, D. M. Giaquinta, S. Guan, V. Markov, D. Poojary, K. Self, H. Turner, and W. H. Weinberg, "Combinatorial discovery of oxidative dehydrogenation catalysts within the Mo—V—Nb—O system.," *Proc. Natl. Acad. Sci. U.S.A.*, vol. 96, no. September, pp. 11077-11080, 1999.—incorporated herein by reference in its entirety]. Isolated mono-vanadates control oxygen release, which decreases $CO_x$ formation and ultimately increase ethylene selectivity. Furthermore, the addition of promoters to catalyst structure can block acid sites which decrease the total acidity (see Table 2). Low acidity contributes to the prevention of cracking of the feed and products on these acid sites and therefore increases ethylene selectivity. This is further supported by reaction results in which methane was not detected.

Table 3 shows the time effect on catalyst conversion and selectivity at a constant temperature of 550° C. It can be noted, that both samples show increasing ethane conversion as time increases. Conversion of the sample $VO_x/La-\gamma Al_2O_3$ was increased from 16.4% at 10 seconds to 23% when reaction time was 50 seconds. With Nb addition, the sample $VO_x$—Nb/La-$\gamma Al_2O_3$ gives higher conversion of 20.15 at 10 seconds and 34.5% at 50 seconds. The increasing trend of ethane conversion can be attributed to the production of more $CO_x$. This can be adhered to oxygen content inside the reaction chamber. The release of oxygen from the catalyst is also a function of reaction time which increases the chances to produce $CO_x$ gasses via combustion reactions.

TABLE 3

Time effect on catalyst performance

| Sample | Time (s) | Ethane conversion (%) | Ethylene selectivity (%) | $CO_2$ Selectivity (%) | CO Selectivity (%) |
|---|---|---|---|---|---|
| $VO_x/La-\gamma Al_2O_3$ | 10 | 16.4 | 71.1 | 54.0 | 30.5 |
|  | 20 | 18.5 | 65.9 | 55.5 | 32.5 |
|  | 30 | 19.8 | 63.8 | 60.0 | 30.7 |
|  | 40 | 20.8 | 61.4 | 61.4 | 31.4 |
|  | 50 | 23.0 | 60.2 | 70.5 | 26.6 |
| $VO_x$—Nb/La—$\gamma Al_2O_3$ | 10 | 20.1 | 85.7 | 52.9 | 23.8 |
|  | 20 | 21.0 | 71.2 | 54.5 | 30.0 |
|  | 30 | 25.0 | 65.4 | 61.4 | 28.8 |
|  | 40 | 28.2 | 62.2 | 68.6 | 26.4 |
|  | 50 | 34.5 | 64.1 | 75.3 | 21.9 |

At temperature = 550° C.

It is important to note that in oxidative dehydrogenation reactions which occur in oxygen free environments, the main source of $O_2$ is from the catalyst, which usually contains oxygen active species. Oxygen active species are in the form of nucleophilic ($O^{2-}$, $O^-$) and electrophilic ($O_2^-$) and the availability of oxygen as a reactant affects ethylene selectivity significantly, and thus as more $O_2$ is released there is a better chance to form $CO_x$. Moreover, from a kinetics standpoint, oxidative dehydrogenation reactions involve several steps, with the rate limiting step being substrate activation. This involves the activation of the C—H bond of ethane, which mainly depends on catalyst and oxygen active species present on the catalyst surface [R. Schl, *Concepts in Selective Oxidation of Small Alkane Molecules*. 2009.—incorporated herein by reference in its entirety].

Figure 17:
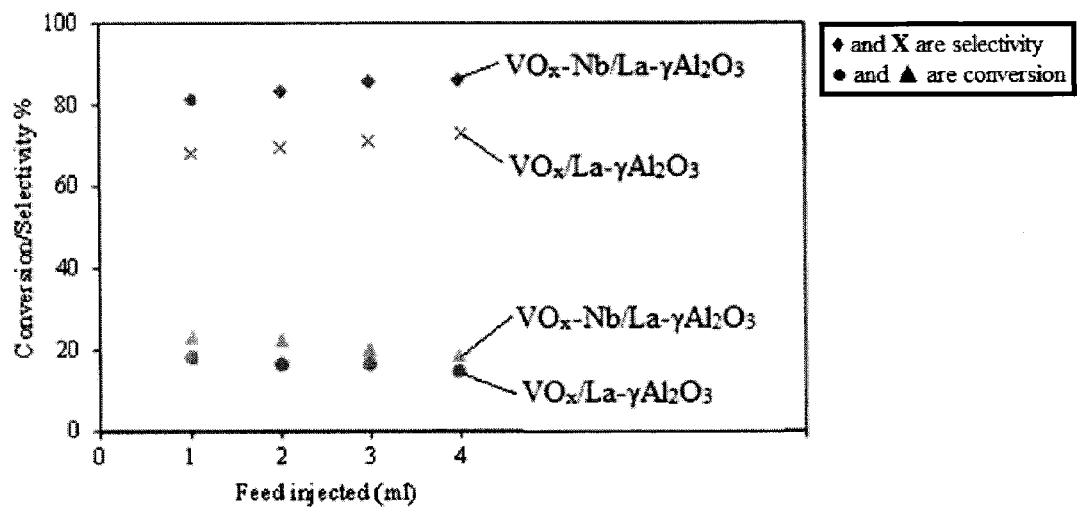
FIG. 17 shows the effect of feed injection on the oxidative dehydrogenation reaction for VO$_x$/La-γAl$_2$O$_3$ catalyst sample and VO$_x$—Nb/La-γAl$_2$O$_3$ catalyst sample at a temperature of 550° C. and a time of 10 s.

The feed injection effect on catalyst conversion and ethylene selectivity was studied by variation of the amount of ethane injected at constant temperature and reaction time. FIG. 17 shows conversion and ethylene selectivity, for both catalyst samples $VO_x/La-\gamma Al_2O_3$ and $VO_x$—Nb/La-$\gamma Al_2O_3$. The conversions are inversely proportional to feed amount injected, primarily due to the increase in the amount of unreacted feed. However, ethylene selectivity was slightly affected by feed increasing from 67.8% to 73.1% for the sample without Nb. Selectivity for the sample with Nb was increased from 83.15 to 86.45% at the 3 mL feed injection in which more active $VO_x$ sites are available for feed dehydrogenation. Furthermore, the presence of excess oxygen inside the reactor increases the combustion reaction and therefore $CO_x$ production. The amount of oxygen that is available for the reaction is controlled mainly by catalyst, but by increasing the feed to oxygen ratio it further decreases the combustion reaction and thus enhances ethylene selectivity.

Figure 18:
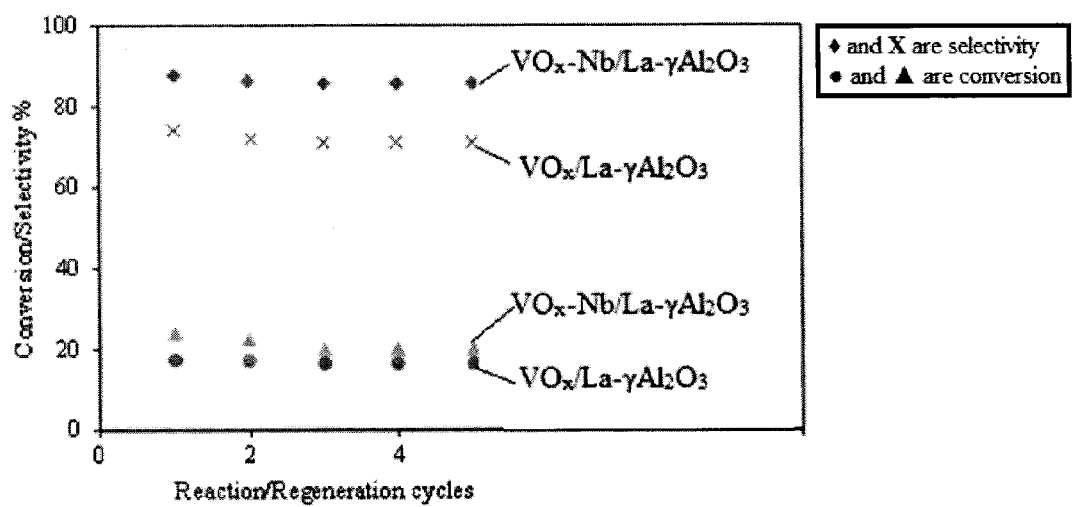
FIG. 18 shows the effect reaction/regeneration cycles on the oxidative dehydrogenation reaction for VO$_x$/La-γAl$_2$O$_3$ catalyst sample and VO$_x$—Nb/La-γAl$_2$O$_3$ catalyst sample at a temperature of 550° C. and a time of 10 s.

FIG. 18 shows repeated reaction-regeneration cycles after separate catalyst regeneration using air at the same reaction temperature for 15 minutes each time. Fresh samples were used for the first run and samples formed by the regeneration with air were used for the following cycles, therefore catalyst performance slightly decreased after the first cycle. Catalyst performance remains stable throughout the cycles in terms of conversion and selectivity, which confirms the catalyst's ability to be regenerated in agreement with the TPR results. The regeneration in this case is oxidation of the reduced vanadium on the support surface, which depends on catalyst stability at high temperature. It has been reported that certain phase transformations occur for the support and the active phases as well where $VO_x$ isolated species agglomerate to form a crystal phase which decreases catalyst performance by decreasing the total number of active sites [E. Nouri, M. Shahmiri, H. R. Rezaie, and F. Talayian, "The effect of alumina content on the structural properties of ZrO 2-Al2O3 unstabilized composite nanopowders," pp. 1-8, 2012.—incorporated herein by reference in its entirety].

Ethane conversion at different fluidization speed is shown in Table 4 at constant reaction time, temperature and catalyst weight. Maintaining fluidized catalyst during reaction time increases mixing of the feed and therefor better access to $VO_x$ sites, which is reflected as an increase in ethane conversion. Furthermore, the sample containing Nb gives higher conversion due to the increased number of isolated VOx sites on the catalyst surface as previously described. Fluidization also enhances catalyst regeneration after the reaction has completed, because again enhanced mixing helps to increase the oxidation process since more vanadium sites are accessible. Most of the previously reported work regarding ethane oxidative dehydrogenation was achieved in fixed-bed reactors and thus lower catalyst activity was obtained.

TABLE 4

Ethane conversion at different fluidization speeds

| Fluidization speed | Conversion % | |
|---|---|---|
| (rpm) | $VO_x/La$—$\gamma Al_2O_3$ | $VO_x$—Nb/La—$\gamma Al_2O_3$ |
| 0 | 5.70 | 8.10 |
| 1000 | 10.4 | 11.1 |
| 2000 | 14.6 | 17.8 |
| 3000 | 16.5 | 20.1 |

At Temperature = 550° C.; feed time = 10 s; catalyst wt. = 0.3 g; and feed = 3 mL In general, $VO_x/La$-$\gamma Al_2O_3$ and VO—Nb/La-$\gamma Al_2O_3$ catalyst samples give good ethylene selectivity (84.7% for samples containing 3% Nb and 71.1% for samples without Nb). Ethane conversion was also increased by Nb introduction from 16.1% to 20.4%, although these conversion values give the highest selectivity at a 10 sec reaction time and a temperature of 550° C. As can be seen from Table 3 higher conversion gives lower ethylene selectivity due to increased formation of $CO_x$ gases. On the whole, ethylene selectivity decreases as conversion increases and also as reaction time increases. Similar studies in oxygen free environments have delivered similar conclusions. It has been established that the high performance catalyst for selective oxidation have isolated active sites to minimize electron influx and to activate reactants (feed and oxygen) to activate the substrate molecule [R. K. Grasselli, S. T. Oyama, and A. M. Gaffney, "3rd World Congress on Oxidation Catalysis R. K. Grasselli, S. T. Oyama, A. M. Gaffney and J. E. Lyons (Editors) 1997 Elsevier Science B. V. 285," pp. 285-294, 1997; and R. K. Brazdil, J. F., Teller, R. G., Grasselli and E. and Kostiner, "sites isolation," ACS Symp. Ser., no. 279, pp. 57-74, 1985.—each incorporated herein by reference in its entirety].

The introduction of niobium (Nb) as a promoter enhanced catalyst performance as previously described. It has been reported that promoters enhance the oxidative dehydrogenation over simple $VO_x$ catalyst by two mechanisms: i) isolation of $VO_x$ species which increases catalyst activity and ii) formation of secondary active metal oxides which also contribute to the oxidative dehydrogenation reaction. Niobium has no significant interactions with vanadium even at high vanadium loadings; however, $Nb_2O_5$ can be found as an isolated species or tending to agglomerate to form a crystal phase. Literature has shown that when $VO_x$ based catalyst have been promoted using Cr, Mo and W metals a significant increase in catalyst performance is obtained. It appears reasonable that the relatively inert $Nb_2O_5$ oxides adsorb ethane in a precursor state that can subsequently supply $VO_x$ sites on the surface in the process of ethane dehydrogenation to ethylene. It has been confirmed that the secondary oxides have greater intrinsic activity for ethane activation than the surface $VO_x$ sites.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method for producing a dehydrogenation catalyst comprising
   a support material comprising alumina modified by lanthanum, and
   a catalytic material disposed on the support material,
      wherein the catalytic material comprises one or more vanadium oxides and niobium as a promoter, and
      wherein the dehydrogenation catalyst comprises 10-20% of the one or more vanadium oxides by weight relative to the total weight of the dehydrogenation catalyst,
   the method comprising:
   mixing lanthanum with alumina to form the support material comprising alumina modified by lanthanum;
   mixing the support material with a solution comprising a vanadium salt and a niobium salt in a solvent to form loaded catalyst precursors;
   reducing the loaded catalyst precursors with $H_2$ gas to form reduced catalyst precursors; and
   oxidizing the reduced catalyst precursors with oxygen to form the dehydrogenation catalyst.

2. A method for dehydrogenating an alkane to a corresponding olefin, comprising:
   flowing the alkane through a reactor comprising a catalyst chamber loaded with a dehydrogenation catalyst at a temperature in the range of 400-800 ° C. to form the corresponding olefin and a reduced catalyst;
   oxidizing the reduced catalyst in an oxygen environment separated from the catalyst chamber to regenerate the dehydrogenation catalyst; and
   repeating the flowing and the oxidizing at least once without a loss in percent conversion of the alkane, a loss in selectivity for the olefin, or both;

wherein the dehydrogenation catalyst comprises:
a support material comprising alumina modified by lanthanum, and
a catalytic material disposed on the support material, wherein the catalytic material comprises one or more vanadium oxides and niobium as a promoter, and
wherein the dehydrogenation catalyst comprises 10-20% of the one or more vanadium oxides by weight relative to the total weight of the dehydrogenation catalyst.

3. A method for dehydrogenating an alkane to a corresponding olefin comprising
flowing the alkane through a reactor comprising a catalyst chamber loaded with a dehydrogenation catalyst at a temperature in the range of 400-800 °C. to form the corresponding olefin and a reduced catalyst,
wherein the reactor is a fluidized bed reactor and the dehydrogenating is performed in an oxygen free environment, and
wherein the dehydrogenation catalyst comprises:
a support material comprising alumina modified by lanthanum, and
a catalytic material disposed on the support material, wherein the catalytic material comprises one or more vanadium oxides and niobium as a promoter, and
wherein the dehydrogenation catalyst comprises 10-20% of the one or more vanadium oxides by weight relative to the total weight of the dehydrogenation catalyst.

4. The method of claim 3, wherein the dehydrogenation catalyst is present at an amount in the range of 0.01-0.5 g per mL of the alkane.

5. The method of claim 3, wherein the alkane is ethane and the method has an ethane conversion of 5-35% at a reaction time of 5-60 seconds and a temperature of 500-600 °C.

6. The method of claim 3, wherein the alkane is ethane and the method has an ethylene selectivity of 60-90% at a reaction time of 5-60 seconds and a temperature of 500-600 °C.

7. The method of claim 3, wherein the dehydrogenation catalyst comprises 1-5% of niobium by weight relative to the total weight of the dehydrogenation catalyst.

8. The method of claim 3, wherein the dehydrogenation catalyst comprises 0.1-3% of lanthanum by weight relative to the total weight of the dehydrogenation catalyst.

9. The method of claim 3, wherein the dehydrogenation catalyst comprises 30-50% of alumina by weight relative to the total weight of the dehydrogenation catalyst.

10. The method of claim 3, wherein the one or more vanadium oxides have the general formula of $V_nO_{2n+1}$, the general formula of $V_nO_{2n-1}$, or both;
wherein n is a whole number greater than zero.

11. The method of claim 3, wherein the one or more vanadium oxides are at least one selected from the group consisting of $V_2O_5$, $VO_2$, and $V_2O_3$.

12. The method of claim 3, wherein the dehydrogenation catalyst comprises at least 50% of $V_2O_5$ by weight relative to the total weight of the one or more vanadium oxides.

13. The method of claim 3, wherein the one or more vanadium oxides form a crystalline phase on the surface of the support material.

14. The method of claim 3, wherein the dehydrogenation catalyst has a BET surface area in the range of 10-50 m²/g.

15. The method of claim 3, wherein the dehydrogenation catalyst has an average particle size in the range of 30-150 μm.

16. The method of claim 3, wherein the dehydrogenation catalyst has an apparent particle density in the range of 1-5 g/cm³.

17. The method of claim 3, wherein the dehydrogenation catalyst has a total acidity in the range of 6-11 mL of $NH_3$ per gram of catalyst.

18. The method of claim 3, wherein the dehydrogenation catalyst is fluidizable and has Class B powder properties in accordance with Geldart particle classification.

* * * * *